US012590323B2

(12) United States Patent
Weber et al.

(10) Patent No.: US 12,590,323 B2
(45) Date of Patent: Mar. 31, 2026

(54) COMPOSITIONS FOR USE IN TREATING AUTOSOMAL DOMINANT BEST1-RELATED RETINOPATHIES

(71) Applicant: Universität Regensburg, Regensburg (DE)

(72) Inventors: Bernhard Weber, Obertraubling (DE); Andrea Milenkovic, Köfering (DE)

(73) Assignee: UNIVERSITÄT REGENSBURG, Regensburg (DE)

( * ) Notice: Subject to any disclaimer, the term of this patent is extended or adjusted under 35 U.S.C. 154(b) by 706 days.

(21) Appl. No.: 17/996,438

(22) PCT Filed: Apr. 20, 2021

(86) PCT No.: PCT/EP2021/060253
§ 371 (c)(1),
(2) Date: Oct. 18, 2022

(87) PCT Pub. No.: WO2021/214006
PCT Pub. Date: Oct. 28, 2021

(65) Prior Publication Data
US 2023/0313235 A1 Oct. 5, 2023

(30) Foreign Application Priority Data

Apr. 20, 2020 (EP) ..................................... 20170327

(51) Int. Cl.
| | |
|---|---|
| *C12N 15/90* | (2006.01) |
| *C12N 9/22* | (2006.01) |
| *C12N 15/11* | (2006.01) |
| *C12N 15/86* | (2006.01) |

(52) U.S. Cl.
CPC .............. *C12N 15/90* (2013.01); *C12N 9/22* (2013.01); *C12N 15/11* (2013.01); *C12N 15/111* (2013.01); *C12N 15/86* (2013.01); *C12N 2310/20* (2017.05); *C12N 2750/14143* (2013.01)

(58) Field of Classification Search
None
See application file for complete search history.

(56) References Cited

U.S. PATENT DOCUMENTS 11,827,879 B2 * 11/2023 Izhar ....................... C12N 15/11

FOREIGN PATENT DOCUMENTS

| | | | | |
|---|---|---|---|---|
| WO | WO 2016/179038 | 11/2016 | | |
| WO | WO 2019/183630 | 9/2019 | | |
| WO | WO-2019183630 A2 * | 9/2019 | ..... | C12Y 301/04035 |
| WO | WO-2020069461 A1 * | 4/2020 | ........... | A61K 48/005 |
| WO | WO 2020/140007 | 7/2020 | | |
| WO | WO 2021/007529 | 1/2021 | | |

OTHER PUBLICATIONS

Fu, Y. et al., "Improving CRISPR-Cas nuclease specificity using truncated guide RNAs," *Nature Biotechnology*, 32.3 (2014): 279-286.
Monteys, A. et al., "CRISPR/Cas9 Editing of the Mutant Huntingtin Allele In Vitro and In Vivo," *Molecular Therapy*, 25.1 (2017): 12-23.
Rabai, A et al., "Allele-Specific CRISPR/Cas9 Correction of a Heterozygous DNM2 Mutation Rescues Centronuclear Myopathy Cell Phenotypes," *Molecular Therapy: Nucleic Acids*, 16 (2019): 246-256.
Ruan, G-X. et al., "CRISPR/Cas9-Mediated Genome Editing as a Therapeutic Approach for Leber Congenital Amaurosis 10," *Molecular Therapy*, 25.2 (2017): 331-341.
Smith, C. et al., "Efficient and Allele-Specific Genome Editing of Disease Loci in Human iPSCs," *Molecular Therapy*, 23.3 (2015): 570-577.
Courtney, D. G. et al., "A Review of Personalized Molecular Medicine for the Treatment of Corneal Disorders," *International Journal of Ophthalmology & Eye Science*, S2:001 (2015): 7-18.
Keough, K. C. et al., "AlleleAnalyzer: a tool for personalized and allele-specific sgRNA design," *Genome Biology*, 20.167 (2019): 1-9.

(Continued)

*Primary Examiner* — Christopher M Babic
(74) *Attorney, Agent, or Firm* — pH IP Law

(57) ABSTRACT

The present invention refers to a sgRNA molecule comprising a targeting domain for specifically targeting a SNP in the BEST1 coding region of a pathologic allele, wherein said targeting domain consists of a sequence selected from the group consisting of SEQ ID NO: 3-8, 41-44, 14-20, 50-52 and 54-55, or a sgRNA molecule combination of specifically defined first and second sgRNA molecules, wherein the first and the second sgRNA molecule each comprise a targeting domain for specifically targeting a SNP in the BEST1 gene coding or non-coding region of a pathologic allele. The present invention also refers to a nucleic acid comprising a sequence that encodes the sgRNA molecule or sgRNA molecule combination and to nucleic acid combinations. The present invention further relates to a recombinant adenovirus-associated virus (AAV) comprising the nucleic acids according to the present invention or recombinant AAV combinations. The sgRNA molecule, the nucleic acid, the recombinant AAV and combinations are useful tools for editing of the target domain in the bestrophin-1 (BEST1) gene to restore BEST1 channel function by e.g. CRISPR/Cas9)-based gene editing. The present invention further relates to the sgRNA molecule, the sgRNA molecule combination, the nucleic acid, the nucleic acid combination, the recombinant AAV and the recombinant AAV combination for use in a method for treatment of the human or animal body by surgery or therapy and for use in method of treating or preventing BEST1-related retinopathies, in particular autosomal dominant BEST1-related retinopathies.

Figure 1:
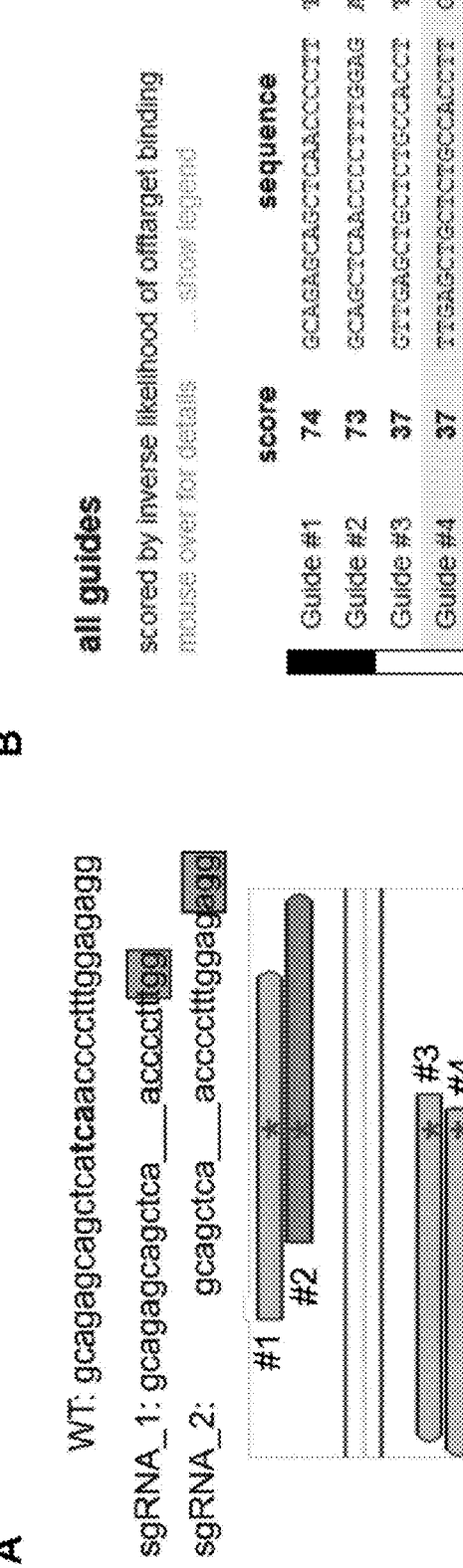

25 Claims, 13 Drawing Sheets
Specification includes a Sequence Listing.

(56)            References Cited

OTHER PUBLICATIONS

PCT International Search Report and Written Opinion issue for International Patent Application No. PCT/EP2021/060253, dated Jul. 17, 2021.

Steyer, B. et al., "Scarless Genome Editing of Human Pluripotent Stem Cells via Transient Puromycin Selection," *Stem Cell Reports*, 10 (2018): 642-654.

* cited by examiner

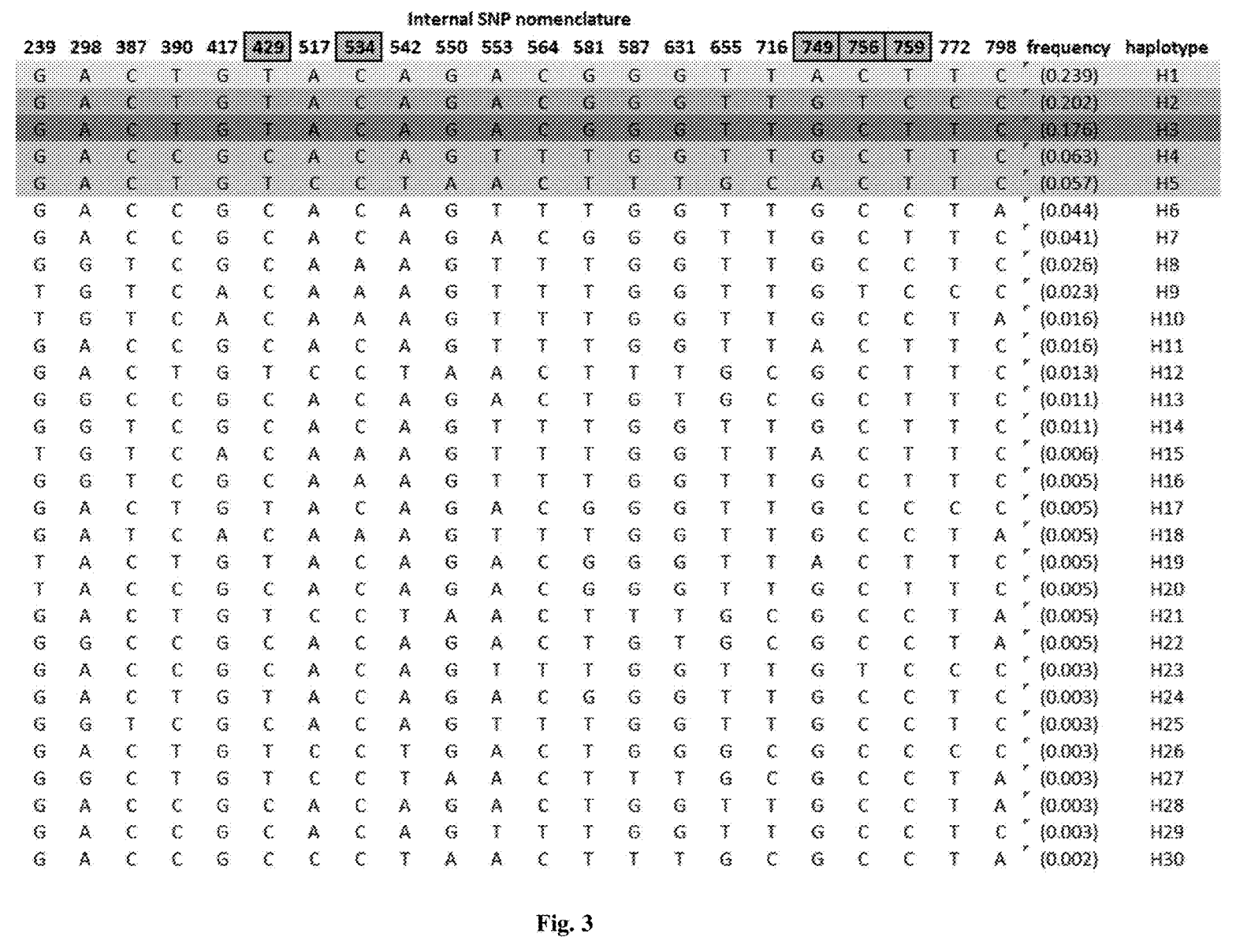

Internal SNP nomenclature

| haplotype | frequency | SNP positions: 239, 298, 387, 390, 417, 429, 517, 534, 542, 550, 553, 564, 581, 587, 631, 655, 716, 749, 755, 759, 772, 798 |
|---|---|---|
| H1 | (0.239) | |
| H2 | (0.202) | |
| H3 | (0.???) | |
| H4 | (0.063) | |
| H5 | (0.057) | |
| H6 | (0.044) | |
| H7 | (0.041) | |
| H8 | (0.026) | |
| H9 | (0.023) | |
| H10 | (0.016) | |
| H11 | (0.016) | |
| H12 | (0.013) | |
| H13 | (0.011) | |
| H14 | (0.011) | |
| H15 | (0.006) | |
| H16 | (0.005) | |
| H17 | (0.005) | |
| H18 | (0.005) | |
| H19 | (0.005) | |
| H20 | (0.005) | |
| H21 | (0.005) | |
| H22 | (0.005) | |
| H23 | (0.003) | |
| H24 | (0.003) | |
| H25 | (0.003) | |
| H26 | (0.003) | |
| H27 | (0.003) | |
| H28 | (0.003) | |
| H29 | (0.003) | |
| H30 | (0.002) | |

Fig. 3

Fig. 4

Fig. 8 n = Seq ID number listed in table 2

Ⓝ = Seq ID number listed in table 2

Ⓝ = Seq ID number listed in table 2

⃝n = Seq ID number listed in table 2

SEQUENCE LISTING

<160> NUMBER OF SEQ ID NOS: 55

<210> SEQ ID NO 1
<211> LENGTH: 18
<212> TYPE: RNA
<213> ORGANISM: Artificial Sequence -continued

```
<220> FEATURE:
<223> OTHER INFORMATION: sgRNA 390T_18nt

<400> SEQUENCE: 1
caagaaggga cuaagaca                                               18

<210> SEQ ID NO 2
<211> LENGTH: 18
<212> TYPE: RNA
<213> ORGANISM: Artificial Sequence
<220> FEATURE:
<223> OTHER INFORMATION: sgRNA 390C_18nt

<400> SEQUENCE: 2
acaaaggagu ccuugucu                                               18

<210> SEQ ID NO 3
<211> LENGTH: 17
<212> TYPE: RNA
<213> ORGANISM: Artificial Sequence
<220> FEATURE:
<223> OTHER INFORMATION: sgRNA 429T_17nt

<400> SEQUENCE: 3
auuaagaacu cgccaua                                                17

<210> SEQ ID NO 4
<211> LENGTH: 19
<212> TYPE: RNA
<213> ORGANISM: Artificial Sequence
<220> FEATURE:
<223> OTHER INFORMATION: sgRNA 429T_19nt_(17)A>C

<400> SEQUENCE: 4
agcuuaagaa cucgccaua                                              19

<210> SEQ ID NO 5
<211> LENGTH: 20
<212> TYPE: RNA
<213> ORGANISM: Artificial Sequence
<220> FEATURE:
<223> OTHER INFORMATION: sgRNA 429C_20nt_(20)A>T

<400> SEQUENCE: 5
uguagcagag caggaagauu                                             20

<210> SEQ ID NO 6
<211> LENGTH: 19
<212> TYPE: RNA
<213> ORGANISM: Artificial Sequence
<220> FEATURE:
<223> OTHER INFORMATION: sgRNA 429C_19nt_(19)G>C

<400> SEQUENCE: 6
cuagcagagc aggaagauu                                              19

<210> SEQ ID NO 7
<211> LENGTH: 18
<212> TYPE: RNA
<213> ORGANISM: Artificial Sequence
<220> FEATURE:
<223> OTHER INFORMATION: sgRNA 534C_18nt

<400> SEQUENCE: 7
aaggaaaugg ggaugagc                                               18
```

-continued

```
<210> SEQ ID NO 8
<211> LENGTH: 18
<212> TYPE: RNA
<213> ORGANISM: Artificial Sequence
<220> FEATURE:
<223> OTHER INFORMATION: sgRNA 534A_18nt

<400> SEQUENCE: 8
uauugcgaca gcuacaua                                            18

<210> SEQ ID NO 9
<211> LENGTH: 17
<212> TYPE: RNA
<213> ORGANISM: Artificial Sequence
<220> FEATURE:
<223> OTHER INFORMATION: sgRNA 517A_17nt

<400> SEQUENCE: 9
ccuuugaaug cauccaa                                             17

<210> SEQ ID NO 10
<211> LENGTH: 17
<212> TYPE: RNA
<213> ORGANISM: Artificial Sequence
<220> FEATURE:
<223> OTHER INFORMATION: sgRNA 517C_17nt

<400> SEQUENCE: 10
uuggcugcau ucaaagg                                             17

<210> SEQ ID NO 11
<211> LENGTH: 18
<212> TYPE: RNA
<213> ORGANISM: Artificial Sequence
<220> FEATURE:
<223> OTHER INFORMATION: sgRNA 542A_18nt

<400> SEQUENCE: 11
gucuaacuuc aguuucuc                                            18

<210> SEQ ID NO 12
<211> LENGTH: 18
<212> TYPE: RNA
<213> ORGANISM: Artificial Sequence
<220> FEATURE:
<223> OTHER INFORMATION: sgRNA 542T_18nt

<400> SEQUENCE: 12
gucuaacuuc aguuucac                                            18

<210> SEQ ID NO 13
<211> LENGTH: 17
<212> TYPE: RNA
<213> ORGANISM: Artificial Sequence
<220> FEATURE:
<223> OTHER INFORMATION: sgRNA 581G_17nt

<400> SEQUENCE: 13
gagggucuuc cgagagc                                             17

<210> SEQ ID NO 14
<211> LENGTH: 19
<212> TYPE: RNA
<213> ORGANISM: Artificial Sequence
<220> FEATURE:
<223> OTHER INFORMATION: sgRNA 749G_20nt
```

-continued

<400> SEQUENCE: 14
uggggcugag gggcgucug                                                    19

<210> SEQ ID NO 15
<211> LENGTH: 19
<212> TYPE: RNA
<213> ORGANISM: Artificial Sequence
<220> FEATURE:
<223> OTHER INFORMATION: sgRNA 749A_20nt

<400> SEQUENCE: 15
uggggcugag gggugucug                                                    19

<210> SEQ ID NO 16
<211> LENGTH: 17
<212> TYPE: RNA
<213> ORGANISM: Artificial Sequence
<220> FEATURE:
<223> OTHER INFORMATION: sgRNA 756C_17nt

<400> SEQUENCE: 16
gcucucagag agcgaug                                                      17

<210> SEQ ID NO 17
<211> LENGTH: 20
<212> TYPE: RNA
<213> ORGANISM: Artificial Sequence
<220> FEATURE:
<223> OTHER INFORMATION: sgRNA 756T_20nt_(17)G>A

<400> SEQUENCE: 17
auuacucuca gagagugaug                                                   20

<210> SEQ ID NO 18
<211> LENGTH: 20
<212> TYPE: RNA
<213> ORGANISM: Artificial Sequence
<220> FEATURE:
<223> OTHER INFORMATION: sgRNA 759T_20nt

<400> SEQUENCE: 18
ucaagugagg aggaaaacug                                                   20

<210> SEQ ID NO 19
<211> LENGTH: 20
<212> TYPE: RNA
<213> ORGANISM: Artificial Sequence
<220> FEATURE:
<223> OTHER INFORMATION: sgRNA 759C_20nt

<400> SEQUENCE: 19
ucaagugagg aggaaaaccg                                                   20

<210> SEQ ID NO 20
<211> LENGTH: 17
<212> TYPE: RNA
<213> ORGANISM: Artificial Sequence
<220> FEATURE:
<223> OTHER INFORMATION: sgRNA I295del_17nt

<400> SEQUENCE: 20
gagcagcuca accccuu                                                      17

<210> SEQ ID NO 21

```
<211> LENGTH: 76
<212> TYPE: RNA
<213> ORGANISM: Artificial Sequence
<220> FEATURE:
<223> OTHER INFORMATION: tracrRNA sequence of sgRNA molecule

<400> SEQUENCE: 21
guuuuagagc uagaaauagc aaguuaaaau aaggcuaguc cguuaucaac uugaaaaagu       60
ggcaccgagu cggugc                                                        76

<210> SEQ ID NO 22
<211> LENGTH: 1367
<212> TYPE: PRT
<213> ORGANISM: Artificial sequence
<220> FEATURE:
<223> OTHER INFORMATION: Synthetic amino acid (SpCas9 endonuclease from
      the Streptococcus pyogenes)

<400> SEQUENCE: 22

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
                20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Ala Thr Arg Leu Lys
        50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300
```

-continued

```
Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
                355                 360                 365

Glu Glu Phe Tyr Lys Phe Ile Lys Pro Ile Leu Glu Lys Met Asp Gly
                370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
                420                 425                 430

Lys Asp Asn Arg Glu Lys Ile Glu Lys Ile Leu Thr Phe Arg Ile Pro
                435                 440                 445

Tyr Tyr Val Gly Pro Leu Ala Arg Gly Asn Ser Arg Phe Ala Trp Met
                450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
                500                 505                 510

Leu Tyr Glu Tyr Phe Thr Val Tyr Asn Glu Leu Thr Lys Val Lys Tyr
                515                 520                 525

Val Thr Glu Gly Met Arg Lys Pro Ala Phe Leu Ser Gly Glu Gln Lys
                530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
                580                 585                 590

Tyr His Asp Leu Leu Lys Ile Ile Lys Asp Lys Asp Phe Leu Asp Asn
                595                 600                 605

Glu Glu Asn Glu Asp Ile Leu Glu Asp Ile Val Leu Thr Leu Thr Leu
                610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
                660                 665                 670

Gln Ser Gly Lys Thr Ile Leu Asp Phe Leu Lys Ser Asp Gly Phe Ala
                675                 680                 685

Asn Arg Asn Phe Met Gln Leu Ile His Asp Asp Ser Leu Thr Phe Lys
                690                 695                 700

Glu Asp Ile Gln Lys Ala Gln Val Ser Gly Gln Gly Asp Ser Leu His
705                 710                 715                 720
```

Glu His Ile Ala Asn Leu Ala Gly Ser Pro Ala Ile Lys Lys Gly Ile
                    725                 730                 735

Leu Gln Thr Val Lys Val Val Asp Glu Leu Val Lys Val Met Gly Arg
        740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                1015                1020

Ser Glu  Gln Glu Ile Gly Lys  Ala Thr Ala Lys Tyr  Phe Phe Tyr
    1025                1030                1035

Ser Asn  Ile Met Asn Phe Phe  Lys Thr Glu Ile Thr  Leu Ala Asn
    1040                1045                1050

Gly Glu  Ile Arg Lys Arg Pro  Leu Ile Glu Thr Asn  Gly Glu Thr
    1055                1060                1065

Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu

-continued

```
                  1130                    1135                    1140

Val Val  Ala Lys Val Glu Lys  Gly Lys Ser Lys Lys  Leu Lys Ser
    1145                    1150                    1155

Val Lys  Glu Leu Leu Gly Ile  Thr Ile Met Glu Arg  Ser Ser Phe
    1160                    1165                    1170

Glu Lys  Asn Pro Ile Asp Phe  Leu Glu Ala Lys Gly  Tyr Lys Glu
    1175                    1180                    1185

Val Lys  Lys Asp Leu Ile Ile  Lys Leu Pro Lys Tyr  Ser Leu Phe
    1190                    1195                    1200

Glu Leu  Glu Asn Gly Arg Lys  Arg Met Leu Ala Ser  Ala Gly Glu
    1205                    1210                    1215

Leu Gln  Lys Gly Asn Glu Leu  Ala Leu Pro Ser Lys  Tyr Val Asn
    1220                    1225                    1230

Phe Leu  Tyr Leu Ala Ser His  Tyr Glu Lys Leu Lys  Gly Ser Pro
    1235                    1240                    1245

Glu Asp  Asn Glu Gln Lys Gln  Leu Phe Val Glu Gln  His Lys His
    1250                    1255                    1260

Tyr Leu  Asp Glu Ile Ile Glu  Gln Ile Ser Glu Phe  Ser Lys Arg
    1265                    1270                    1275

Val Ile  Leu Ala Asp Ala Asn  Leu Asp Lys Val Leu  Ser Ala Tyr
    1280                    1285                    1290

Asn Lys  His Arg Asp Lys Pro  Ile Arg Glu Gln Ala  Glu Asn Ile
    1295                    1300                    1305

Ile His  Leu Phe Thr Leu Thr  Asn Leu Gly Ala Pro  Ala Ala Phe
    1310                    1315                    1320

Lys Tyr  Phe Asp Thr Thr Ile  Asp Arg Lys Arg Tyr  Thr Ser Thr
    1325                    1330                    1335

Lys Glu  Val Leu Asp Ala Thr  Leu Ile His Gln Ser  Ile Thr Gly
    1340                    1345                    1350

Leu Tyr  Glu Thr Arg Ile Asp  Leu Ser Gln Leu Gly  Gly Asp
    1355                    1360                    1365
```

```
<210> SEQ ID NO 23
<211> LENGTH: 4101
<212> TYPE: DNA
<213> ORGANISM: Artificial sequence
<220> FEATURE:
<223> OTHER INFORMATION: Synthetic oligonucleotide (SpCas9 endonuclease
      from the Streptococcus pyogenes)

<400> SEQUENCE: 23
gacaagaagt acagcatcgg cctggacatc ggcaccaact ctgtgggctg ggccgtgatc      60
accgacgagt acaaggtgcc cagcaagaaa ttcaaggtgc tgggcaacac cgaccggcac     120
agcatcaaga agaacctgat cggagccctg ctgttcgaca gcggcgaaac agccgaggcc     180
acccggctga agagaaccgc cagaagaaga tacaccagac ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggacg aggtggccta ccacgagaag taccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga accccgacaa cagcgacgtg     540
gacaagctgt tcatccagct ggtgcagacc tacaaccagc tgttcgagga aaaccccatc     600
aacgccagcg gcgtggacgc caaggccatc ctgtctgcca gactgagcaa gagcagacgg     660
```

```
ctggaaaatc tgatcgccca gctgcccggc gagaagaaga atggcctgtt cggcaacctg        720
attgccctga gcctgggcct gacccccaac ttcaagagca acttcgacct ggccgaggat        780
gccaaactgc agctgagcaa ggacacctac gacgacgacc tggacaacct gctggcccag        840
atcggcgacc agtacgccga cctgtttctg gccgccaaga acctgtccga cgccatcctg        900
ctgagcgaca tcctgagagt gaacaccgag atcaccaagg cccccctgag cgcctctatg        960
atcaagagat acgacgagca ccaccaggac ctgaccctgc tgaaagctct cgtgcggcag       1020
cagctgcctg agaagtacaa agagattttc ttcgaccaga gcaagaacgg ctacgccggc       1080
tacattgacg gcggagccag ccaggaagag ttctacaagt tcatcaagcc catcctggaa       1140
aagatggacg gcaccgagga actgctcgtg aagctgaaca gagaggacct gctgcggaag       1200
cagcggacct tcgacaacgg cagcatcccc caccagatcc acctgggaga gctgcacgcc       1260
attctgcggc ggcaggaaga ttttttaccca ttcctgaagg acaaccggga aaagatcgag       1320
aagatcctga ccttccgcat cccctactac gtgggccctc tggccagggg aaacagcaga       1380
ttcgcctgga tgaccagaaa gagcgaggaa accatcaccc cctggaactt cgaggaagtg       1440
gtggacaagg gcgcttccgc ccagagcttc atcgagcgga tgaccaactt cgataagaac       1500
ctgcccaacg agaaggtgct gcccaagcac agcctgctgt acgagtactt caccgtgtat       1560
aacgagctga ccaaagtgaa atacgtgacc gagggaatga aaagcccgc cttcctgagc       1620 ggcgagcaga aaaaggccat cgtggacctg ctgttcaaga ccaaccggaa agtgaccgtg       1680
aagcagctga agaggacta cttcaagaaa atcgagtgct tcgactccgt ggaaatctcc       1740
ggcgtggaag atcggttcaa cgcctccctg ggcacatacc acgatctgct gaaaattatc       1800
aaggacaagg acttcctgga caatgaggaa aacgaggaca ttctggaaga tatcgtgctg       1860
accctgacac tgtttgagga cagagagatg atcgaggaac ggctgaaaac ctatgcccac       1920
ctgttcgacg acaaagtgat gaagcagctg aagcggcgga gatacaccgg ctggggcagg       1980
ctgagccgga agctgatcaa cggcatccgg gacaagcagt ccggcaagac aatcctggat       2040
ttcctgaagt ccgacggctt cgccaacaga aacttcatgc agctgatcca cgacgacagc       2100
ctgaccttta agaggacat ccagaaagcc caggtgtccg gccagggcga tagcctgcac       2160
gagcacattg ccaatctggc cggcagcccc gccattaaga agggcatcct gcagacagtg       2220
aaggtggtgg acgagctcgt gaaagtgatg ggccggcaca gcccagaa catcgtgatc       2280 gaaatggcca gagagaacca gaccacccag aagggacaga agaacagccg cgagagaatg       2340
aagcggatcg aagagggcat caaagagctg ggcagccaga tcctgaaaga acacccgtg       2400 gaaacacccc agctgcagaa cgagaagctg tacctgtact acctgcagaa tgggcgggat       2460
atgtacgtgg accaggaact ggacatcaac cggctgtccg actacgatgt ggaccatatc       2520
gtgcctcaga gctttctgaa ggacgactcc atcgacaaca aggtgctgac cagaagcgac       2580
aagaaccggg gcaagagcga caacgtgccc tccgaagagg tcgtgaagaa gatgaagaac       2640
tactggcggc agctgctgaa cgccaagctg attacccaga aaagttcga caatctgacc       2700 aaggccgaga gaggcggcct gagcgaactg gataaggccg gcttcatcaa gagacagctg       2760
gtggaaaccc ggcagatcac aaagcacgtg gcacagatcc tggactcccg gatgaacact       2820
aagtacgacg agaatgacaa gctgatccgg gaagtgaaag tgatcaccct gaagtccaag       2880
ctggtgtccg atttccggaa ggatttccag ttttacaaag tgcgcgagat caacaactac       2940
caccacgccc acgacgccta cctgaacgcc gtcgtgggaa ccgccctgat caaaaagtac       3000
```

-continued

```
cctaagctgg aaagcgagtt cgtgtacggc gactacaagg tgtacgacgt gcggaagatg      3060
atcgccaaga gcgagcagga aatcggcaag gctaccgcca agtacttctt ctacagcaac      3120
atcatgaact ttttcaagac cgagattacc ctggccaacg gcgagatccg gaagcggcct      3180
ctgatcgaga caaacggcga aaccggggag atcgtgtggg ataagggccg ggattttgcc      3240
accgtgcgga aagtgctgag catgccccaa gtgaatatcg tgaaaaagac cgaggtgcag      3300
acaggcggct tcagcaaaga gtctatcctg cccaagagga acagcgataa gctgatcgcc      3360
agaaagaagg actgggaccc taagaagtac ggcggcttcg acagccccac cgtggcctat      3420
tctgtgctgg tggtggccaa agtggaaaag ggcaagtcca agaaactgaa gagtgtgaaa      3480
gagctgctgg ggatcaccat catggaaaga agcagcttcg agaagaatcc catcgacttt      3540
ctggaagcca agggctacaa agaagtgaaa aaggacctga tcatcaagct gcctaagtac      3600
tccctgttcg agctggaaaa cggccggaag agaatgctgg cctctgccgg cgaactgcag      3660
aagggaaacg aactggccct gccctccaaa tatgtgaact tcctgtacct ggccagccac      3720
tatgagaagc tgaagggctc cccgaggat aatgagcaga aacagctgtt tgtggaacag      3780
cacaagcact acctggacga gatcatcgag cagatcagcg agttctccaa gagagtgatc      3840
ctggccgacg ctaatctgga caaagtgctg tccgcctaca acaagcaccg ggataagccc      3900
atcagagagc aggccgagaa tatcatccac ctgtttaccc tgaccaatct gggagcccct      3960
gccgccttca gtactttga caccaccatc gaccggaaga ggtacaccag caccaaagag      4020
gtgctggacg ccaccctgat ccaccagagc atcaccggcc tgtacgagac acggatcgac      4080
ctgtctcagc tgggaggcga c                                                4101
```

<210> SEQ ID NO 24
<211> LENGTH: 508
<212> TYPE: DNA
<213> ORGANISM: Artificial Sequence
<220> FEATURE:
<223> OTHER INFORMATION: Full-length CMV promoter sequence

<400> SEQUENCE: 24

```
cgttacataa cttacggtaa atggcccgcc tggctgaccg cccaacgacc cccgcccatt        60
gacgtcaata atgacgtatg ttcccatagt aacgccaata gggactttcc attgacgtca       120
atgggtggag tatttacggt aaactgccca cttggcagta catcaagtgt atcatatgcc       180
aagtacgccc cctattgacg tcaatgacgg taaatggccc gcctggcatt atgcccagta       240
catgacctta tgggactttc ctacttggca gtacatctac gtattagtca tcgctattac       300
catggtgatg cggttttggc agtacatcaa tgggcgtgga tagcggtttg actcacgggg       360
atttccaagt ctccaccca ttgacgtcaa tgggagtttg ttttggcacc aaaatcaacg       420
ggactttcca aaatgtcgta acaactccgc cccattgacg caaatgggcg gtaggcgtgt       480
acggtgggag gtctatataa gcagagct                                          508
```

<210> SEQ ID NO 25
<211> LENGTH: 100
<212> TYPE: DNA
<213> ORGANISM: Artificial Sequence
<220> FEATURE:
<223> OTHER INFORMATION: Minimal CMV promoter sequence (100 bp)

<400> SEQUENCE: 25

```
ccaaaatcaa cgggactttc caaaatgtcg taacaactcc gccccattga cgcaaatggg        60
cggtaggcgt gtacggtggg aggtctatat aagcagagct                             100
```

-continued

```
<210> SEQ ID NO 26
<211> LENGTH: 159
<212> TYPE: DNA
<213> ORGANISM: Artificial Sequence
<220> FEATURE:
<223> OTHER INFORMATION: Minimal CMV promoter sequence (159 bp)

<400> SEQUENCE: 26
gactcacggg gatttccaag tctccacccc attgacgtca atgggagttt gtttttggcac      60 caaaatcaac gggactttcc aaaatgtcgt aacaactccg ccccattgac gcaaatgggc     120
ggtaggcgtg tacggtggga ggtctatata agcagagct                            159

<210> SEQ ID NO 27
<211> LENGTH: 215
<212> TYPE: DNA
<213> ORGANISM: Artificial Sequence
<220> FEATURE:
<223> OTHER INFORMATION: Full-length H1 promoter sequence (215 bp)

<400> SEQUENCE: 27
gaacgctgac gtcatcaacc cgctccaagg aatcgcgggc ccagtgtcac taggcgggaa      60
cacccagcgc gcgtgcgccc tggcaggaag atggctgtga gggacagggg agtggcgccc     120
tgcaatattt gcatgtcgct atgtgttctg ggaaatcacc ataaacgtga aatgtctttg     180
gatttgggaa tcgtataaga actgtatgag accac                                215

<210> SEQ ID NO 28
<211> LENGTH: 95
<212> TYPE: DNA
<213> ORGANISM: Artificial Sequence
<220> FEATURE:
<223> OTHER INFORMATION: Minimal H1 promoter sequence (95 bp)

<400> SEQUENCE: 28
tgcaatattt gcatgtcgct atgtgttctg ggaaatcacc ataaacgtga aatgtctttg      60
gatttgggaa tcgtataaga actgtatgag accac                                 95

<210> SEQ ID NO 29
<211> LENGTH: 241
<212> TYPE: DNA
<213> ORGANISM: Artificial Sequence
<220> FEATURE:
<223> OTHER INFORMATION: Full-length U6 promoter sequence (241 bp)

<400> SEQUENCE: 29
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
c                                                                     241

<210> SEQ ID NO 30
<211> LENGTH: 99
<212> TYPE: DNA
<213> ORGANISM: Artificial Sequence
<220> FEATURE:
<223> OTHER INFORMATION: Minimal U6 promoter sequence (99 bp)

<400> SEQUENCE: 30
```

-continued

```
gagggcctat ttcccatgat tccttcatag actatcatat gcttaccgta acttgaaagt          60
atttcgattt cttggcttta tatatcttgt ggaaaggac                                99

<210> SEQ ID NO 31
<211> LENGTH: 49
<212> TYPE: DNA
<213> ORGANISM: Artificial Sequence
<220> FEATURE:
<223> OTHER INFORMATION: Minimal poly(A) sequence (49 bp)

<400> SEQUENCE: 31
aataaaagat ctttattttc attagatctg tgtgttggtt ttttgtgtg                     49

<210> SEQ ID NO 32
<211> LENGTH: 31
<212> TYPE: DNA
<213> ORGANISM: unknown
<220> FEATURE:
<223> OTHER INFORMATION: WT

<400> SEQUENCE: 32
gcagagcagc tcatcaaccc ctttggagag g                                        31

<210> SEQ ID NO 33
<211> LENGTH: 23
<212> TYPE: DNA
<213> ORGANISM: unknown
<220> FEATURE:
<223> OTHER INFORMATION: sgRNA_1

<400> SEQUENCE: 33
gcagagcagc tcaacccctt tgg                                                  23

<210> SEQ ID NO 34
<211> LENGTH: 23
<212> TYPE: DNA
<213> ORGANISM: unknown
<220> FEATURE:
<223> OTHER INFORMATION: sgRNA_2

<400> SEQUENCE: 34
gcagctcaac ccctttggag agg                                                  23

<210> SEQ ID NO 35
<211> LENGTH: 23
<212> TYPE: DNA
<213> ORGANISM: unknown
<220> FEATURE:
<223> OTHER INFORMATION: Guide #1

<400> SEQUENCE: 35
gcagagcagc tcaacccctt tgg                                                  23

<210> SEQ ID NO 36
<211> LENGTH: 23
<212> TYPE: DNA
<213> ORGANISM: unknown
<220> FEATURE:
<223> OTHER INFORMATION: Guide #2

<400> SEQUENCE: 36
gcagctcaac ccctttggag agg                                                  23

<210> SEQ ID NO 37
<211> LENGTH: 23
```

```
<212> TYPE: DNA
<213> ORGANISM: unknown
<220> FEATURE:
<223> OTHER INFORMATION: Guide #3

<400> SEQUENCE: 37
gttgagctgc tctgccacct tgg                                                    23

<210> SEQ ID NO 38
<211> LENGTH: 23
<212> TYPE: DNA
<213> ORGANISM: unknown
<220> FEATURE:
<223> OTHER INFORMATION: Guide #4

<400> SEQUENCE: 38
ttgagctgct ctgccacctt ggg                                                    23

<210> SEQ ID NO 39
<211> LENGTH: 20
<212> TYPE: RNA
<213> ORGANISM: Artificial Sequence
<220> FEATURE:
<223> OTHER INFORMATION: sgRNA 390T_20nt

<400> SEQUENCE: 39
uacaagaagg gacuaagaca                                                        20

<210> SEQ ID NO 40
<211> LENGTH: 19
<212> TYPE: RNA
<213> ORGANISM: Artificial Sequence
<220> FEATURE:
<223> OTHER INFORMATION: sgRNA 390C_19nt

<400> SEQUENCE: 40
cacaaaggag uccuugucu                                                         19

<210> SEQ ID NO 41
<211> LENGTH: 20
<212> TYPE: RNA
<213> ORGANISM: Artificial sequence
<220> FEATURE:
<223> OTHER INFORMATION: sgRNA 429T_20nt

<400> SEQUENCE: 41
aagauuaaga acucgccaua                                                        20

<210> SEQ ID NO 42
<211> LENGTH: 19
<212> TYPE: RNA
<213> ORGANISM: Artificial Sequence
<220> FEATURE:
<223> OTHER INFORMATION: sgRNA 534C_19nt

<400> SEQUENCE: 42
gaaggaaaug gggaugagc                                                         19

<210> SEQ ID NO 43
<211> LENGTH: 19
<212> TYPE: RNA
<213> ORGANISM: Artificial Sequence
<220> FEATURE:
<223> OTHER INFORMATION: sgRNA 534C_20nt

<400> SEQUENCE: 43
```
cgaaggaaau ggggaugag                                              19

<210> SEQ ID NO 44
<211> LENGTH: 20
<212> TYPE: RNA
<213> ORGANISM: Artificial Sequence
<220> FEATURE:
<223> OTHER INFORMATION: sgRNA 534A_20nt

<400> SEQUENCE: 44
uguauugcga cagcuacaua                                            20

<210> SEQ ID NO 45
<211> LENGTH: 20
<212> TYPE: RNA
<213> ORGANISM: Artificial Sequence
<220> FEATURE:
<223> OTHER INFORMATION: sgRNA 517A_20nt

<400> SEQUENCE: 45
gauccuuuga augcauccaa                                            20

<210> SEQ ID NO 46
<211> LENGTH: 20
<212> TYPE: RNA
<213> ORGANISM: Artificial Sequence
<220> FEATURE:
<223> OTHER INFORMATION: sgRNA 517C_20nt

<400> SEQUENCE: 46
gauccuuuga augcagccaa                                            20

<210> SEQ ID NO 47
<211> LENGTH: 20
<212> TYPE: RNA
<213> ORGANISM: Artificial Sequence
<220> FEATURE:
<223> OTHER INFORMATION: sgRNA 542A_20nt

<400> SEQUENCE: 47
acgucuaacu ucaguuucuc                                            20

<210> SEQ ID NO 48
<211> LENGTH: 20
<212> TYPE: RNA
<213> ORGANISM: Artificial Sequence
<220> FEATURE:
<223> OTHER INFORMATION: sgRNA 542T_20nt

<400> SEQUENCE: 48
acgucuaacu ucaguuucac                                            20

<210> SEQ ID NO 49
<211> LENGTH: 19
<212> TYPE: RNA
<213> ORGANISM: Artificial Sequence
<220> FEATURE:
<223> OTHER INFORMATION: sgRNA 581G_20nt

<400> SEQUENCE: 49
ccugaggguc uuccgagag                                             19

<210> SEQ ID NO 50
<211> LENGTH: 17
<212> TYPE: RNA
<213> ORGANISM: Artificial Sequence -continued

```
<220> FEATURE:
<223> OTHER INFORMATION: sgRNA 756T_17nt

<400> SEQUENCE: 50
gcucucagag agugaug                                                       17

<210> SEQ ID NO 51
<211> LENGTH: 20
<212> TYPE: RNA
<213> ORGANISM: Artificial Sequence
<220> FEATURE:
<223> OTHER INFORMATION: sgRNA I295del_20nt

<400> SEQUENCE: 51
gcagagcagc ucaaccccuu                                                    20

<210> SEQ ID NO 52
<211> LENGTH: 18
<212> TYPE: RNA
<213> ORGANISM: Artificial Sequence
<220> FEATURE:
<223> OTHER INFORMATION: sgRNA I295del_18nt

<400> SEQUENCE: 52
agagcagcuc aaccccuu                                                      18

<210> SEQ ID NO 53
<211> LENGTH: 17
<212> TYPE: RNA
<213> ORGANISM: Artificial Sequence
<220> FEATURE:
<223> OTHER INFORMATION: sgRNA 517C_17nt

<400> SEQUENCE: 53
ccuuugaaug cagccaa                                                       17

<210> SEQ ID NO 54
<211> LENGTH: 20
<212> TYPE: RNA
<213> ORGANISM: Artificial Sequence
<220> FEATURE:
<223> OTHER INFORMATION: sgRNA 749G_20nt

<400> SEQUENCE: 54
uggggcugag gggcgucugu                                                    20

<210> SEQ ID NO 55
<211> LENGTH: 20
<212> TYPE: RNA
<213> ORGANISM: Artificial Sequence
<220> FEATURE:
<223> OTHER INFORMATION: sgRNA 749A_20nt

<400> SEQUENCE: 55
uggggcugag gggugucugu                                                    20
```

COMPOSITIONS FOR USE IN TREATING AUTOSOMAL DOMINANT BEST1-RELATED RETINOPATHIES

CROSS-REFERENCE TO RELATED APPLICATIONS

This application is a national phase application under 35 U.S.C. § 371 of International Application No. PCT/EP2021/060253, filed Apr. 20, 2021, the entire contents of which are hereby incorporated by reference, and which claims benefit of priority to European Application No. 20170327.9, filed Apr. 20, 2020.

INCORPORATION OF SEQUENCE LISTING

The sequence listing that is contained in the file named "DEBEP0162US_update2_ST25.txt", which is 29,589 bytes (as measured in Microsoft Windows®) and created on Sep. 16, 2025, is filed herewith by electronic submission, and is incorporated by reference herein.

The present invention refers to a sgRNA molecule comprising a targeting domain for specifically targeting a SNP in the BEST1 coding region of a pathologic allele, wherein said targeting domain consists of a sequence selected from the group consisting of SEQ ID NO: 3-8, 41-44, 14-20, 50-52, and 54-55, or a sgRNA molecule combination of specifically defined first and second sgRNA molecules, wherein the first and the second sgRNA molecule each comprise a targeting domain for specifically targeting a SNP in the BEST1 gene coding or non-coding region of a pathologic allele. The present invention also refers to a nucleic acid comprising a sequence that encodes the sgRNA molecule or sgRNA molecule combination and to nucleic acid combinations. The present invention further relates to a recombinant adenovirus-associated virus (AAV) comprising the nucleic acids according to the present invention or recombinant AAV combinations. The sgRNA molecule, the nucleic acid, the recombinant AAV and combinations are useful tools for editing of the target domain in the bestrophin-1 (BEST1) gene to restore BEST1 channel function by e.g. CRISPR/Cas9-based gene editing. The present invention further relates to the sgRNA molecule, the sgRNA molecule combination, the nucleic acid, the nucleic acid combination, the recombinant AAV and the recombinant AAV combination for use in a method for treatment of the human or animal body by surgery or therapy and for use in method of treating or preventing BEST1-related retinopathies, in particular autosomal dominant BEST1-related retinopathies.

The BEST1 (MIM 607854) gene encodes an integral membrane protein which is localized most prominently to the basolateral membrane of the human retinal pigment epithelium (RPE). At least four distinct retinopathies, collectively called the bestrophinopathies, have been linked to pathologic BEST1 mutations including the autosomal dominant Best macular dystrophy (Marquardt et al., 1998; Petrukhin et al., 1998), the autosomal dominant vitreoretinochoroidopathy (ADVIRC; MIM 607854) (Yardley et al., 2004) as well as the autosomal recessive bestrophinopathy (ARB; MIM 611809). Finally, a phenotype known as pattern dystrophy can be separated from the typical Best macular dystrophy and is inherited as an autosomal dominant trait with a specific single mutation in BEST1, p.Ala243Val (Boon et al. 2009; Khan et al. 2018).

Best macular dystrophy, the most common form of the bestrophinopathies, is a progressive retinal disorder primarily affecting the macular area of the posterior pole. Prevalence is estimated to be between 1:5 000 and approximately 1:50 000 in northern Sweden and Denmark, respectively. In 2017 the prevalence of Best macular dystrophy in Minnesota, USA, was reported to be in a range between 1:7 000 to 1:21 000. Assuming a European population of approximately 500 million people between 10.000 to 100.000 cases could be expected in Europe and about the same number for the United States/Canada.

The disease is characterized by an accumulation of lipofuscin-like material and subretinal fluids causing the formation of serous retinal detachment and lesions that classically resemble in the initial stage an "egg yolk" (=vitelliform). In contrast to Best macular dystrophy, ADVIRC is a rare peripheral chorioretinal pigmentary disorder with an estimated prevalence of 1:1.000.000. A common end point for both, Best macular dystrophy and ADVIRC, is a substantial degree of photoreceptor cell loss eventually leading to vision impairment. So far, more than 250 independent disease-causing BEST1 mutations have been reported in the Human Gene Mutation Database. Dominant-negative mutations in BEST1 are causative for Best macular dystrophy and ADVIRC, thereby affecting BEST1 localization, ion gating properties and protein stability. Consequently, these functional impairments result in loss of BEST1 chloride transport function.

To date, there is no treatment for the various types of bestrophinopathies. This is in contrast to a number of other retinal dystrophies for which clinical trials are underway, specifically for gene replacement therapies. In December 2017, the Food and Drug Administration (FDA) approved Luxturna, the first AAV vector gene therapy that treats patients with a rare form of inherited early vision loss called Leber Congenital Amaurosis (LCA), caused by loss-of-function mutations in the RPE65 gene. Subretinal injections of AAV particles carrying constructs encoding wildtype RPE65 were shown to be safe and effective in patients, without causing adverse effects.

X-ray structures of chicken BEST1-Fab complexes revealed that the eukaryotic BEST1 channel is a pentameric structure composed of homomeric BEST1 subunits. This channel is thought to be involved in volume regulation and/or calcium homeostasis. Assuming equal expression of wildtype and mutant protein in a heterozygous Best macular dystrophy or ADVIRC patient, oligomerization of mutant and wildtype subtypes results in as little as ~ 3% of functional channels consisting of five wildtype subunits. Therefore, allele-specific silencing of the mutant allele while leaving the wildtype allele intact appears an effective therapeutic approach to ablate dominant-negative or gain-of-function gene expression and thus could greatly increase the proportion of functional channel units per cell. Initial reports have suggested that CRISPR/Cas9-based gene editing could serve as a specific tool to abolish mutant mRNA and protein expression (Long et al., 2016).

The CRISPR/Cas9 bacterial system allows targeting of any site within the human genome via a 17-20-nucleotide (nt) sequence of a specific single guide RNA (sgRNA). The Cas9/sgRNA complex binds and cleaves a defined DNA sequence leading to genomic insertions or deletions (indels) as a consequence of the cellular error-prone nonhomologous end joining (NHEJ) repair. This results in early stop codons in roughly two-thirds of indel alleles. A special feature of this system is that Cas9 nucleases require the recognition of a sequence motif called the protospacer adjacent motif (PAM) located 3' of the sgRNA binding site. The absence of such a PAM sequence results in the inability of Cas9 to cleave the DNA target and is therefore a limiting factor in addressing a particular nucleotide sequence.

Utilizing the specificity of the CRISPR/Cas9 genome editing system single point mutations associated with autosomal dominant diseases have been targeted recently in an allele-specific manner in patient-derived human induced pluripotent stem cells (hiPSCs) (Smith et al., 2015; Yamamoto et al., 2017), patient fibroblasts (Monteys et al., 2017; Rabai et al., 2019) and cancer cell lines (Koo et al., 2017; Lee et al., 2018). Furthermore, this approach has already successfully been translated into two animal models of human diseases, the P23H Rhodopsin knock-in mouse model for autosomal dominant retinitis pigmentosa (adRP) (Giannelli et al., 2018) and the Beethoven mouse for the autosomal dominant inherited form of deafness (Gao et al., 2018), in both cases resulting in significant phenotypic improvements.

In general, allele-specific targeting of the Cas9 nuclease activity to the disease allele can be accomplished in several ways: (1) by generating sgRNAs that include the disease-associated nucleotide in the 17 to 20 nt sgRNA sequence (mutation-based approach) in order to delete the pathologic BEST1 allele and ablate dominant-negative or gain-of-function gene expression; and (2) by targeting common single nucleotide polymorphisms (SNPs) in cis to the mutation (haplotype-based approach) using (i) a single sgRNAs for heterozygous variants in the coding sequence or (ii) two distinct intronic SNPs spanning a large genomic region thereby deleting one or several exons of the gene. The challenge of an allele-specific approach is to design the most efficient and specific sgRNAs that exclusively suppress the pathologic BEST1 allele while leaving the wildtype allele intact and by showing no off-target effects in the genome.

A recent study investigated CRISPR/Cas9 treatment options for patients with Leber congenital amaurosis type 10 (LCA10) (Ruan et al., 2017), a severe form of inherited retinal disorders with early onset of symptoms in the first year of life. In a cellular model of LCA10 the authors showed that sgRNA pairs coupled with SpCas9 efficiently deleted a specific deep intronic mutation located in intron 26 of the human CEP290 gene thereby preventing the splicing of the mutant cryptic exon and restoring wildtype CEP290 expression. In July 2018, Editas Medicine, Inc. (Cambridge, MA), one of the leading gene editing companies, published a first patent application for four sgRNAs targeting the particular intronic mutation in the CEP290 gene (patent application: US 2018/0195058 A1). In December 2018, the same company received authorization from the US Food and Drug Administration (FDA) to launch a clinical trial for the treatment of LCA patients. Four months later, the open-label, single ascending dose study was started to evaluate safety and efficacy (ClinicalTrials.gov Identifier: NCT03872479). The treatment "EDIT-101" is administered as a subretinal injection of AAV particles to deliver the gene editing tools to photoreceptor cells.

In general, AAV-mediated delivery is currently the gold standard for cargo delivery into retinal cells and has repeatedly been demonstrated to be safe and effective for gene replacement applications in patients, without causing adverse effects. Only recently, the FDA approved a first AAV vector gene therapy (Luxturna) for the treatment of LCA2 patients. In November 2018, Novartis Pharmaceuticals Corp. announced EU approval for Luxturna.

WO 2019/183630 discloses specific BEST1 sgRNA sequences and teaches that these sequences can be used to treat autosomal dominant diseases such as retinopathy caused by BEST1 mutations. As outlined in WO 2019/

183630 this can be done by using one gRNA or a combination of two sgRNAs in order to cleave at two different sites to be able to delete part of the disease-causing gene. When using one gRNA it should be targeted to a SNP in the dominant disease-related gene according to WO 2019/183630. WO 2019/183630 does not teach that said one gRNA should be targeted to a SNP in a coding region (exon) of the pathologic allele. When using two sgRNAs, WO 2019/183630 discloses a first sgRNAs specifically targeting a SNP in the non-coding region of the pathologic allele and a second sgRNA that hybridizes to an intron in the dominant disease-related gene thereby inducing a biallelic double-strand break in intronic sequences. In the past, it was assumed that a repair of a biallelic double-strand break in a non-coding region remains without consequences for gene expression. Nevertheless, with the discovery of non-coding RNAs and other non-coding essential regulatory elements, our knowledge about the functional significance of non-coding sequences in the human genome is increasing steadily with enormous impact on our further understanding of the regulation of the human genome. Therefore, there might be side effects resulting from approach of 2019/183630 as one cannot appreciate at present what such an approach might do to the expression of BEST1 or other genes in cis or trans position.

The problem to be solved by the present invention is to provide effective and particular safe means for treating autosomal dominant BEST1-related retinophathies by gene editing using CRISPR/Cas9-mediated methods to suppress mutant BEST1 expression.

Software tools available nowadays are helpful to predict efficacy and specificity of sgRNA sequences, although solely at a length of 20 nucleotides. There is no prediction tool available so far to predict truncated (20nt) sgRNAs which often possess a higher sequence specificity and thus an improved locus-specific CRISPR/Cas9 nuclease efficacy over the original 20nt sgRNA. The higher sequence specificity results in less genome-wide off-targets.

A further problem to be solved by the present invention is to provide means for CRISPR/Cas9 mediated methods having a higher sequence specificity and thus an improved locus-specific CRISPR/Cas9 nuclease efficacy over the original 20nt sgRNA and thereby reducing the risk of genome-wide off-targets and, therefore, further increasing the efficacy and safety.

The problem underlying the present invention is solved by the subject matter defined in the claims.

The following figures serve to illustrate the invention.

FIG. 1 shows the computational prediction of sgRNAs targeting the BEST1 1295del mutation. (A) Prediction of 4 sgRNAs to target the BEST1-1295del (884-886delTCA) locus by the "Optimised CRISPR Design Tool" (Zhang, MIT Broad Institute). (B) Specificity scores for 20nt guides #1-4 taking into account putative off-target binding. Scores range from 0 to 100. Black bar=score>50 (high quality), White bar=score<50 (low quality); * position of 1295del in the 20nt sgRNA sequence. Of note, the scoring algorithm for on-target prediction is restricted to 20nt sgRNAs.

Figure 2:
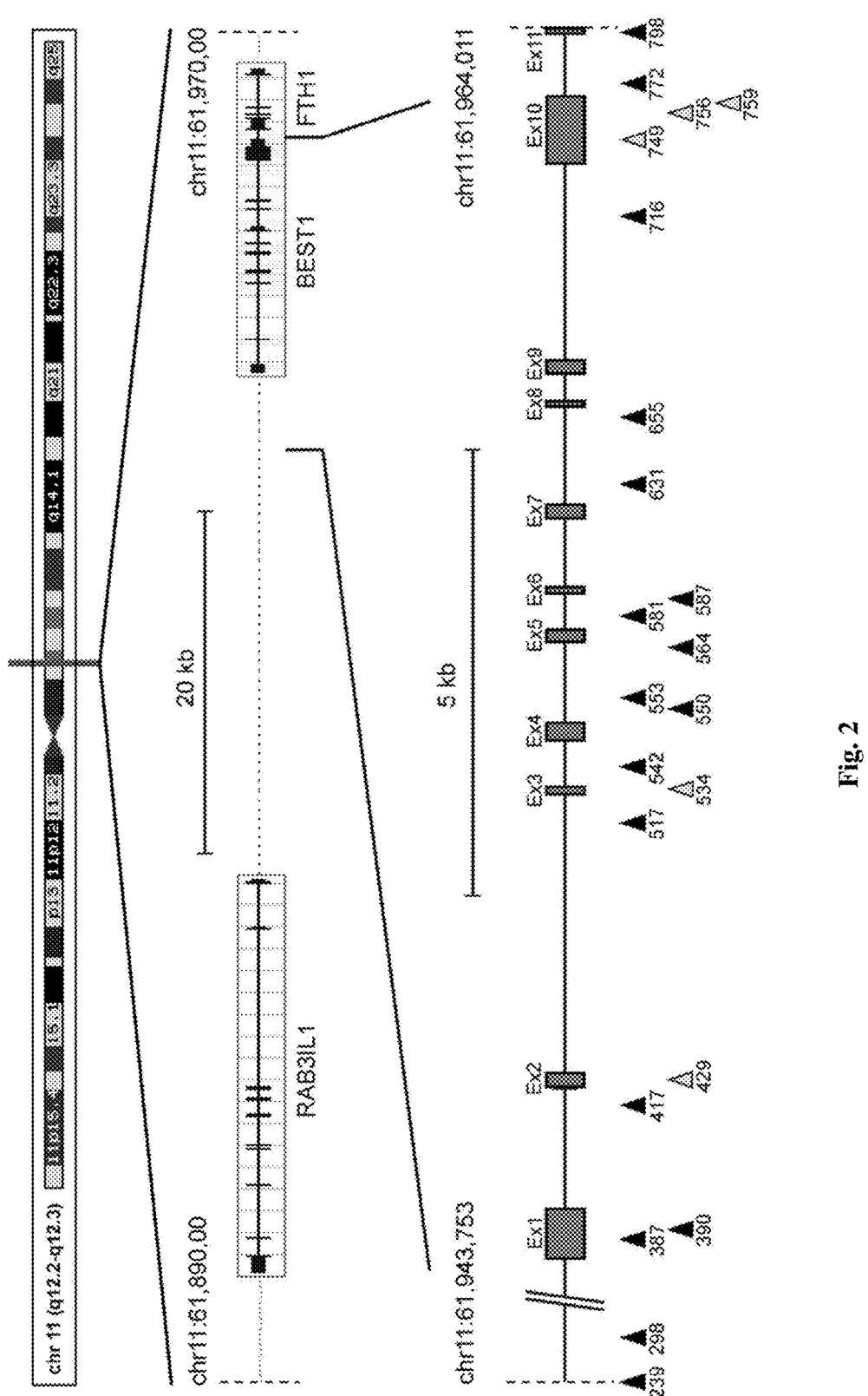

FIG. 2 shows an analysis of the genomic BEST1 region analyzed and the position of 22 SNPs selected by in silico analysis for targeting. Genes: interacting protein like 1 (RAB31IL1), ferritin heavy chain 1 (FTH1), BEST1; Ex: coding exons 1-11; triangle: position of the selected SNPs within the BEST1 locus; triangles (light grey): SNPs within coding sequences of BEST1.

FIG. 3 shows haplotype frequencies at the BEST1 locus in the European population estimated from 22 SNPs identified at the BEST1 locus. Shaded grey lines: haplotype frequency>5%; framed squares: SNPs in BEST1 coding region.

Figure 4:
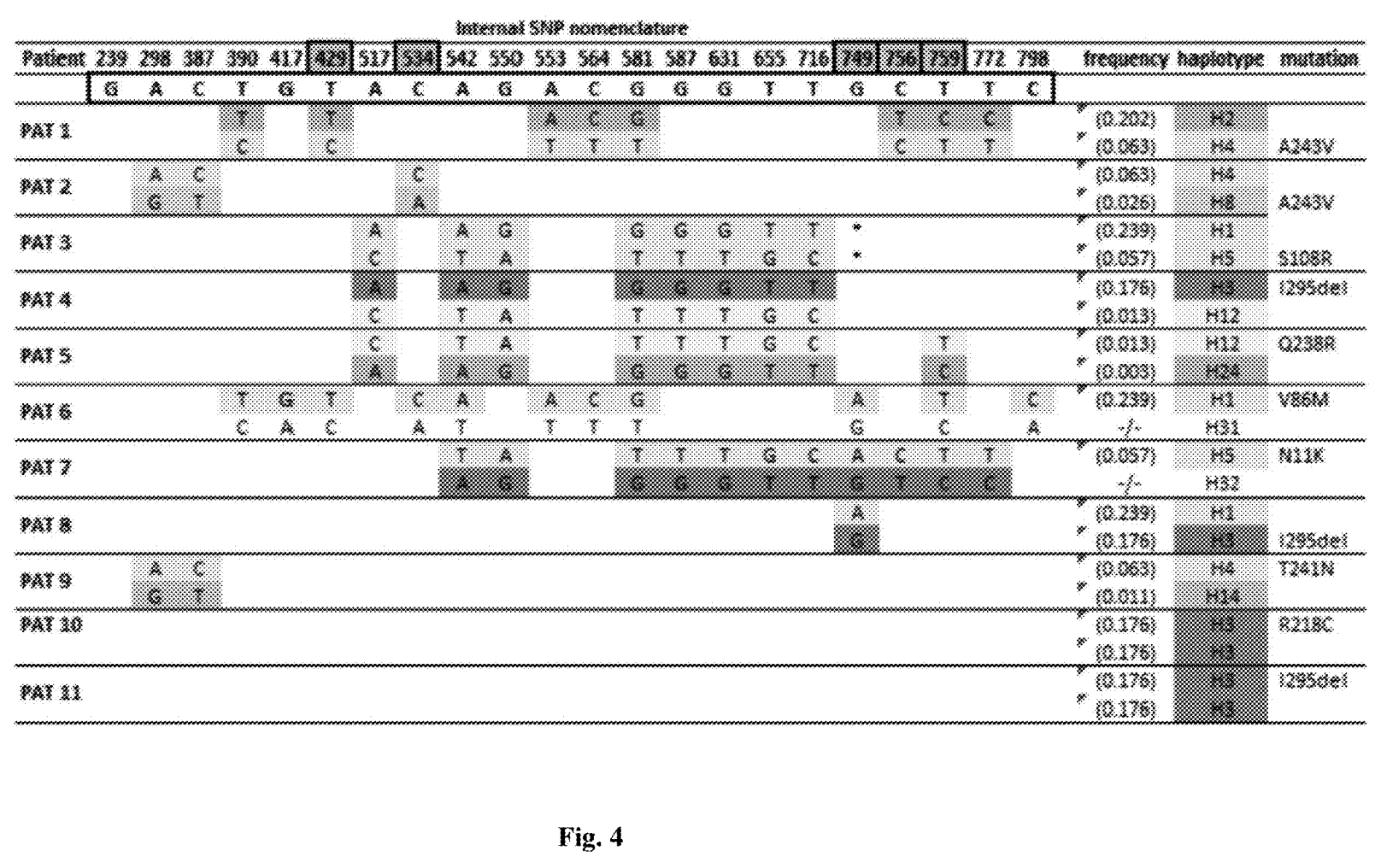

FIG. 4 shows haplotype frequencies of the Best macular dystrophy patient cohort estimated from 22 identified SNPs at the BEST1 locus. Second line: nucleotide sequence within bold frame; framed squares: SNPs in BEST1 coding region; only heterozygous chromosomes are specified, non-filled positions correspond to the reference sequence; * nucleotide with lower frequency; haplotype numbers correspond to that of the European population as shown in FIG. 3.

Figure 5:
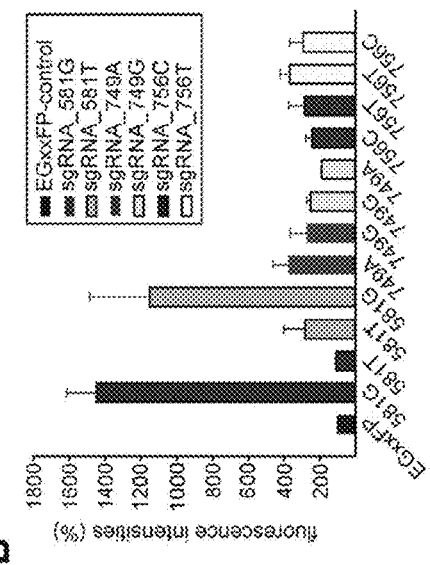
Figure 5:
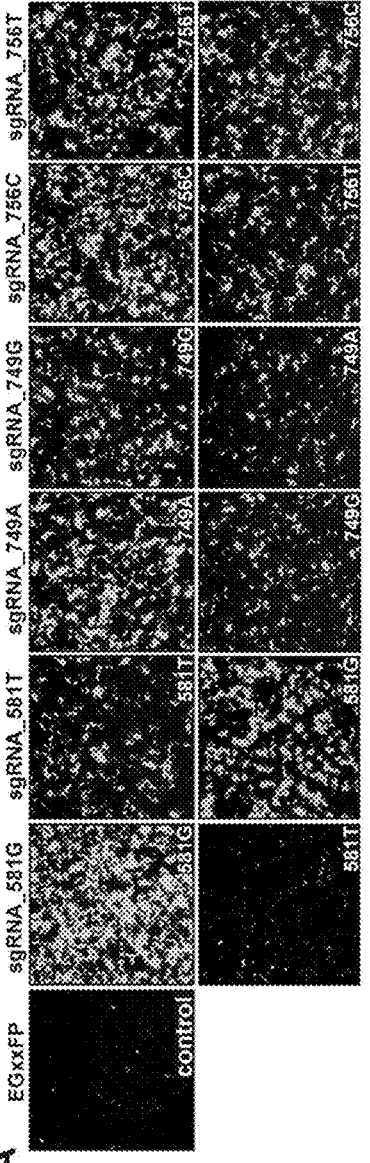

FIG. 5 shows the evaluation of computationally designed sgRNAs. More specifically, the evaluation of allele-specific SpCas9 cleavage of designated sgRNAs in HEK293T cells is shown. (A) Immunofluorescence imaging of HEK293T cells transfected with pCAG-EGxxFP (empty vector) (left), pCAG-EG_on-target_FP+sgRNA_X_20nt (upper row) or pCAG-EG_non-target_FP+sgRNA_X_20nt (lower row); (B) Quantification of (A) relative to basal fluorescence intensities of pCAG-EGxxFP (n=3-4).

Figure 6:
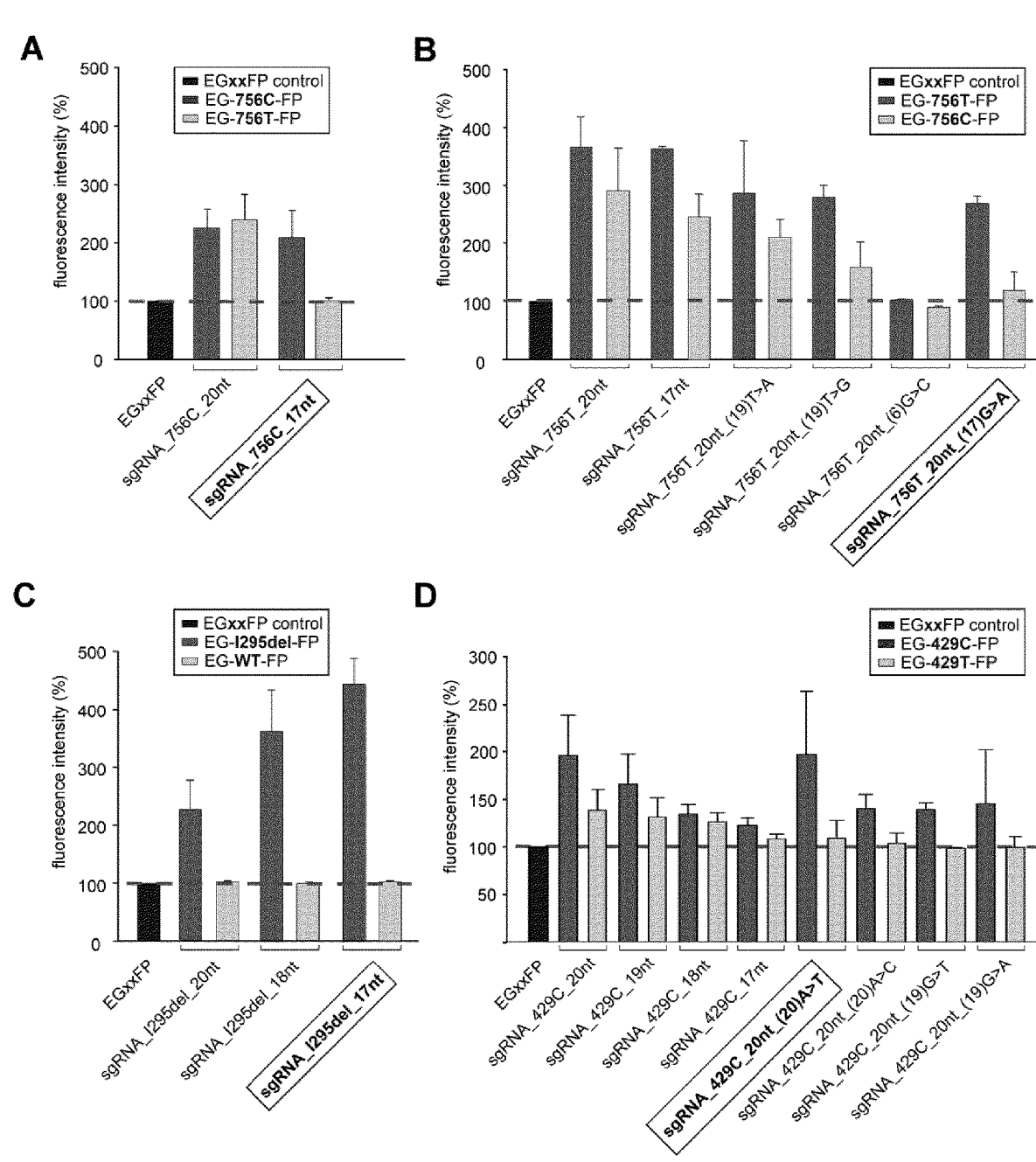

FIG. 6 shows the optimization of computationally designed sgRNAs. More specifically, the optimization of sgRNA specificity in HEK293T cells is shown. Quantification of EGFP fluorescence intensities relative to the empty pCAG-EGxxFP vector by plate reader measurements. HEK293T cells were transfected with pCAG-EG_on-target_FP+sgRNA_X or pCAG-EG_non-target_FP+sgRNA_X after sgRNA truncation (A-D) and additional sequence modifications (B and D); framed sgRNA showing highest specificity and efficiency for the indicated SNP variant.

Figure 7:
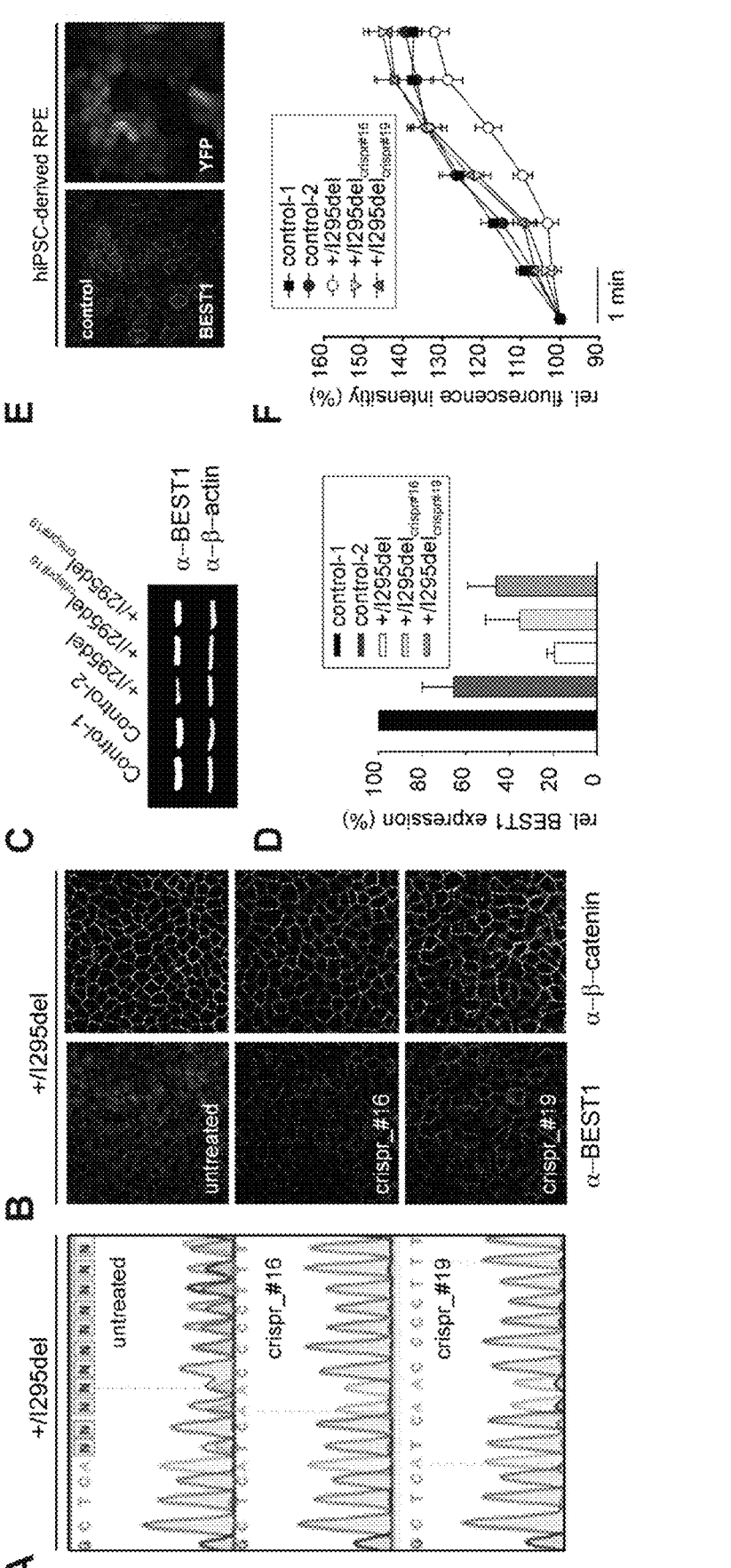

FIG. 7 shows the effect of CRISPR/SpCas9 in-vitro gene editing in Best macular dystrophy-patient derived hiPSC-RPE cells. More specifically, the effect of allele-specific gene editing in Best macular dystrophy-associated hiPSC-RPE cells heterozygous for the 1295del mutation is shown. (A) Sequence traces at the 1295del locus from untreated and edited cDNA samples. (B) Confocal immunofluorescence images of untreated and edited hiPSC-RPE cells after 6 weeks growth on transwell filters. Beta-catenin served as control for monolayer integrity. (C) Representative Western blot image of control, untreated and edited hiPSC-RPE cell lysates. (D) Quantification of BEST1 protein expression from (C) normalized to beta-actin from the same blots. (E) Representative fluorescence image of control hiPSC-RPE cells expressing YFP after lentiviral transduction. (F) Fluorescence intensities of YFP after a 6 min iodide pre-incubation step (time point 0) in a time-course of 0 to 6 min after application of Cl– containing solution; *=P<0.05 relative to untreated patient sample.

Figure 8:
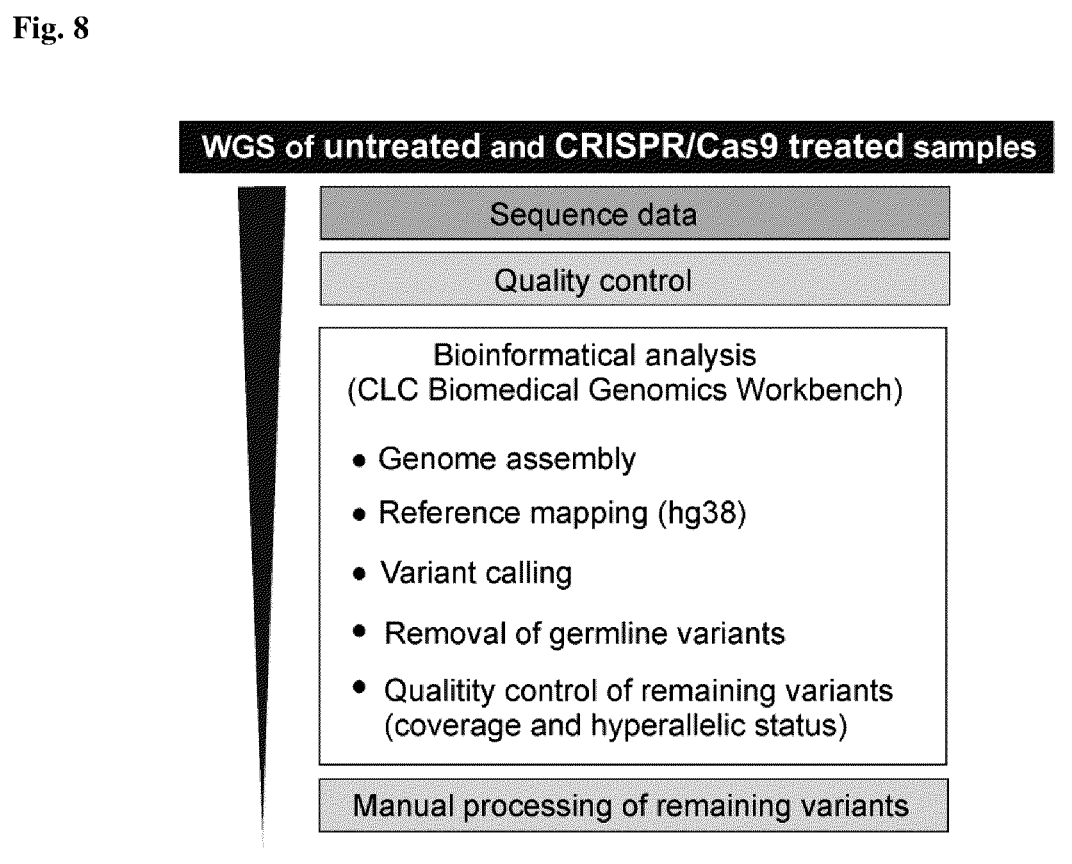

FIG. 8 shows a bioinformatics workflow for processing whole-genome sequencing data. More specifically, the filtering process of sequencing data from whole genome sequencing is shown. A presentation of the filtering process of genetic variants found by whole-genome sequencing in untreated and CRISPR/Cas9-treated samples is given.

Figure 9:
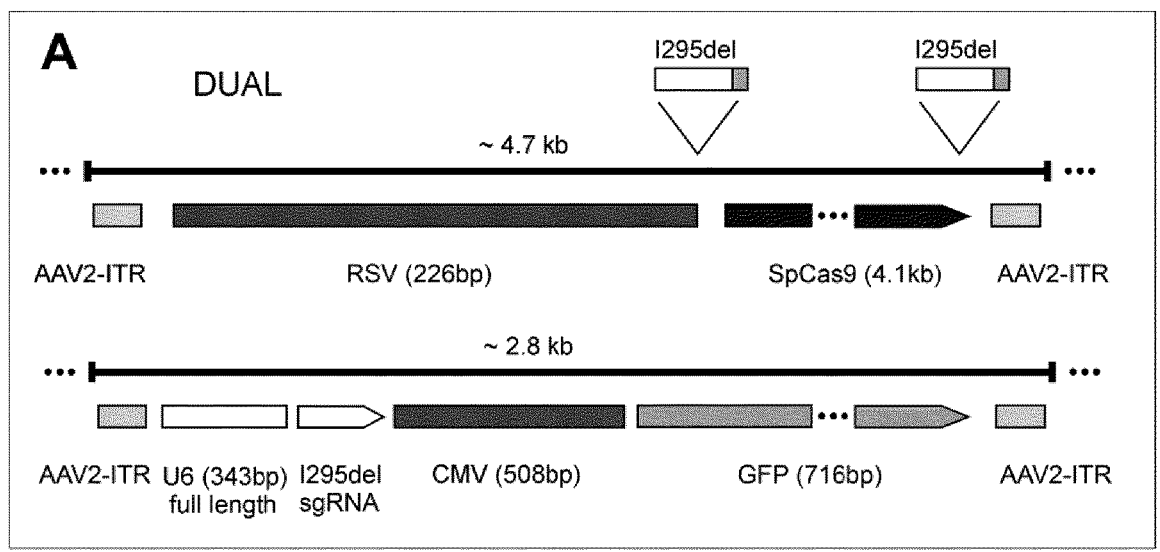
Figure 9:
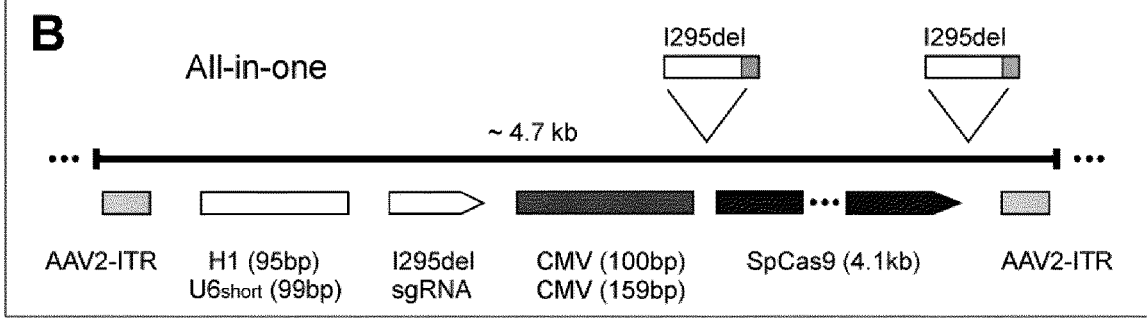
Figure 9:
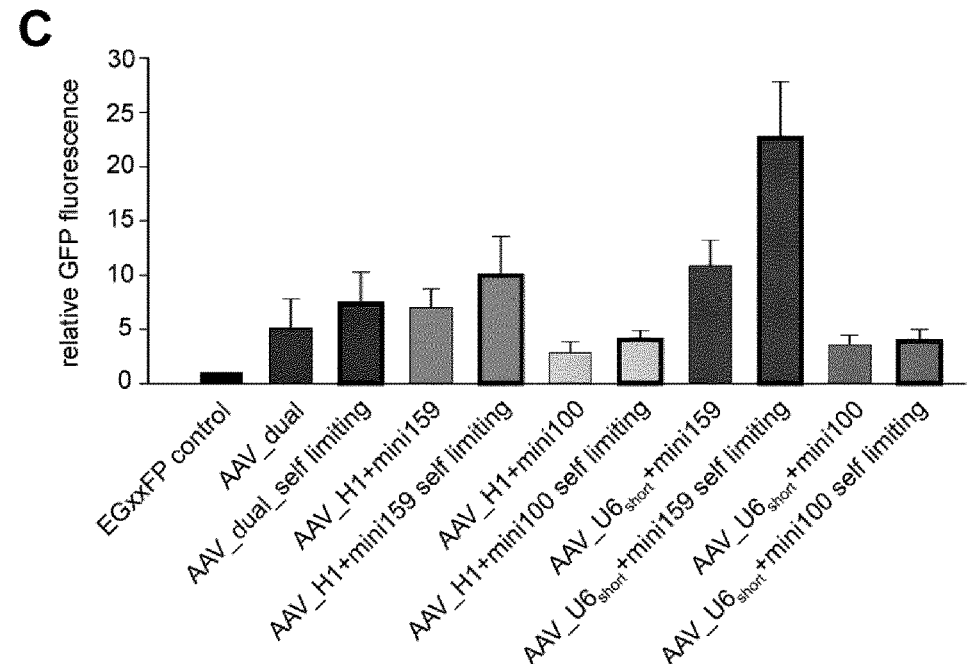

FIG. 9 shows the generation of a self-limiting "all-in-one" AAV vector. More specifically, the effect of promoter type and sequence length on CRISPR/SpCas9 cleavage performance is shown. Schematic presentation of AAV constructs with indicated promoter type and sequence lengths for (A) dual AAV vector delivery (SpCas9 and sgRNA are engineered into two separate AAV expression plasmids (pAAV—RSV-SpCas9+pAAV-U6-sgRNA-GFP and (B) single AAV vector delivery (SpCas9 and sgRNA are engineered into one AAV expression plasmid). (C) Quantification of EGFP fluorescence intensities relative to the empty pCAG-EGxxFP vector by plate reader measurements. HEK293T cells were co-transfected with spCAG-EG_1295del_FP and AAV plasmids containing sgRNA_1295del17nt and SpCas9 under the control of indicated promoters.

Figure 10:
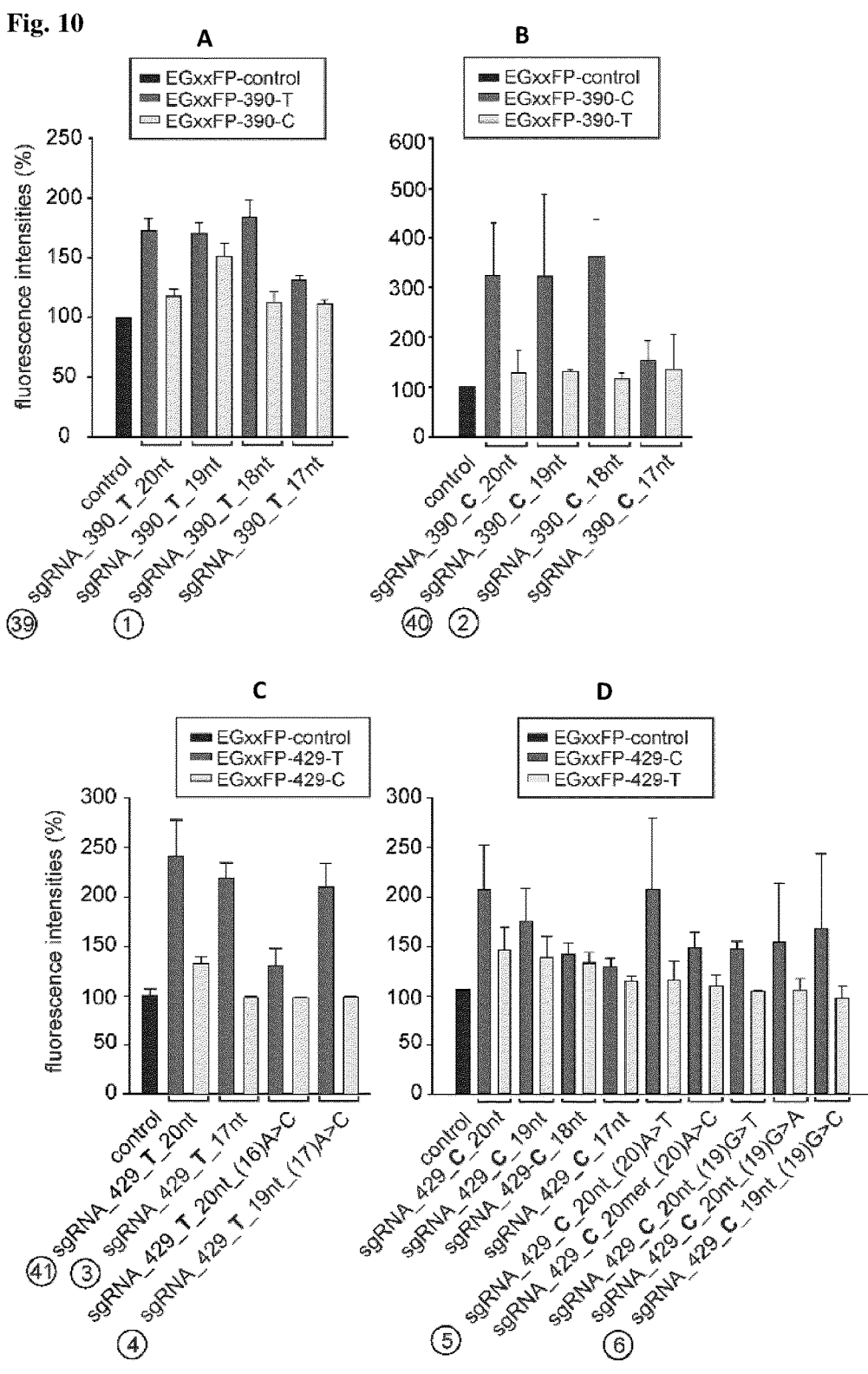

FIG. 10 shows the optimization of computationally designed sgRNAs. More specifically, the optimization of sgRNA specificity in HEK293T cells is shown. Quantification of EGFP fluorescence intensities relative to the empty pCAG-EGxxFP vector by plate reader measurements. HEK293T cells were transfected with pCAG-EG_on-target_FP+sgRNA_X or pCAG-EG_non-target_FP+sgRNA_X. X=SNP-variant 390T (A), SNP-variant 390C (B), SNP-variant 429T (C) and SNP-variant 429C (D). sgRNAs marked by a number in a circle showed the desired effect of strong CRISPR/Cas9 activity on the pathologic allele while the wildtype allele remained uneffected.

Figure 11:
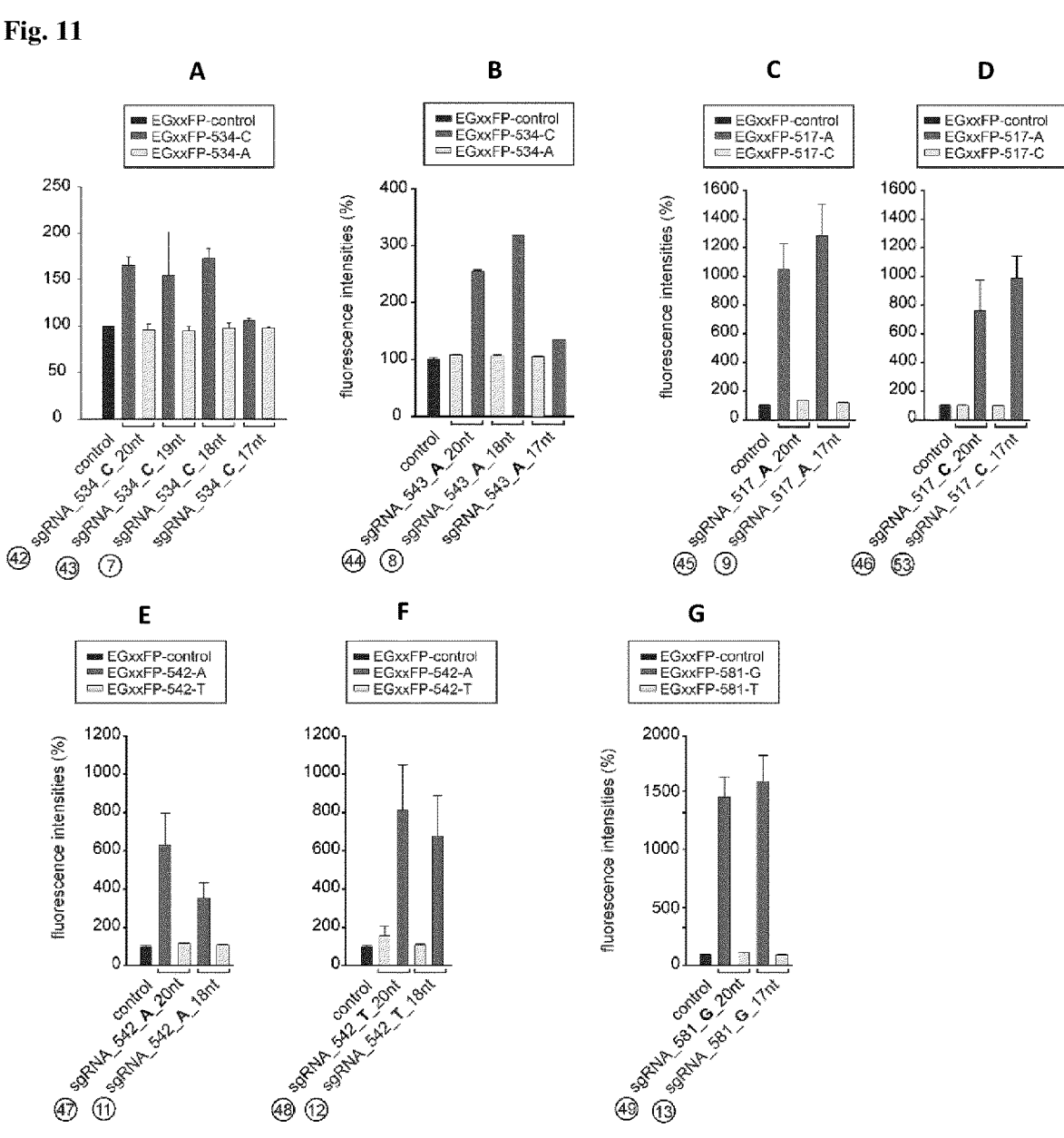

FIG. 11 shows the optimization of computationally designed sgRNAs. More specifically, the optimization of sgRNA specificity in HEK293T cells is shown. Quantification of EGFP fluorescence intensities relative to the empty pCAG-EGxxFP vector by plate reader measurements. HEK293T cells were transfected with pCAG-EG_on-target_FP+sgRNA_X or pCAG-EG_non-target_FP+sgRNA_X. X=SNP-variant 534C (A), SNP-variant 543A (B), SNP-variant 517A (C), SNP-variant 517C (D), SNP-variant 542A (E), SNP-variant 542T (F) and SNP-variant 581G (G). sgRNAs marked by a number in a circle showed the desired effect of strong CRISPR/Cas9 activity on the pathologic allele while the wildtype allele remained uneffected.

Figure 12:
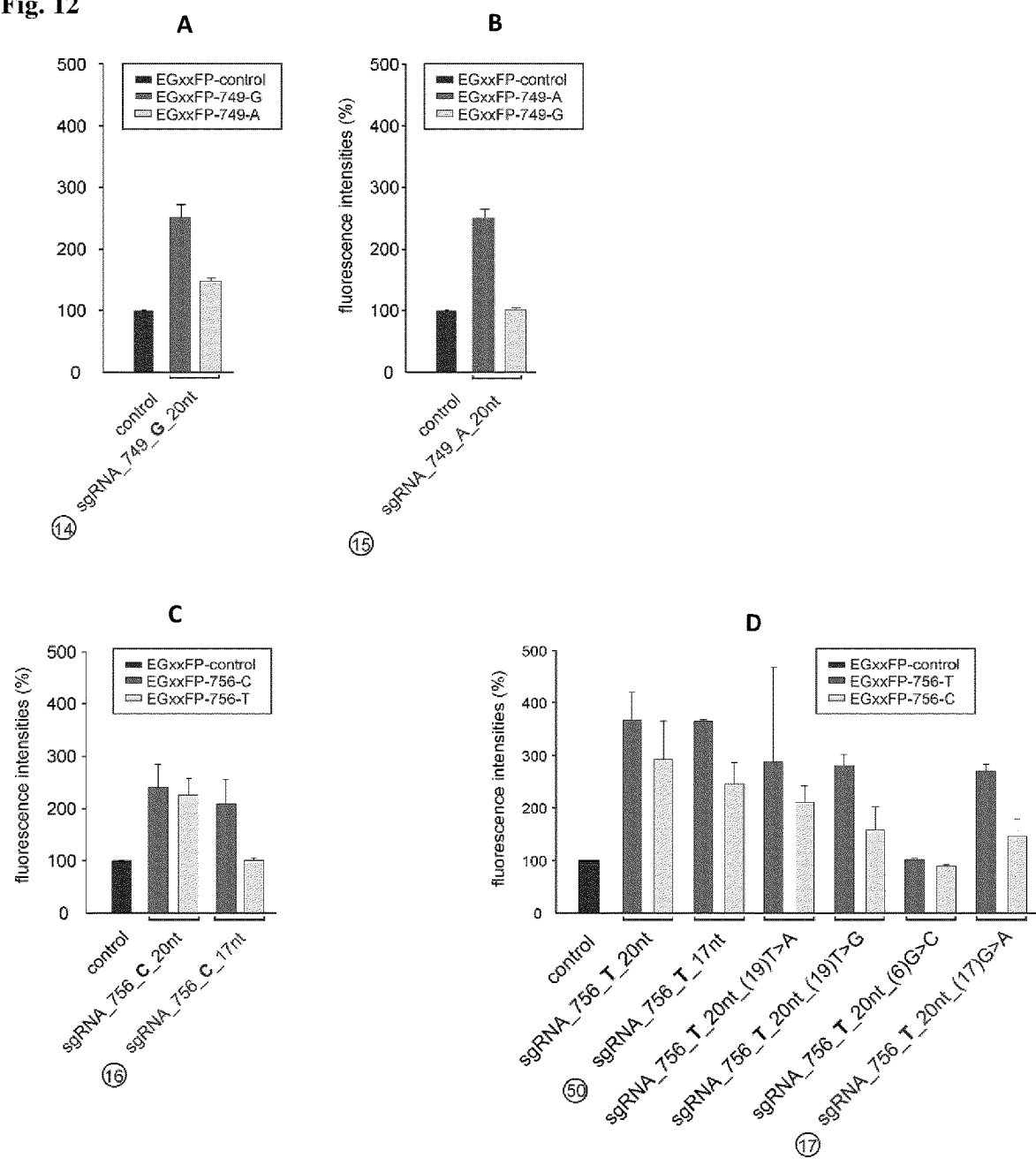

FIG. 12 shows the optimization of computationally designed sgRNAs. More specifically, the optimization of sgRNA specificity in HEK293T cells is shown. Quantification of EGFP fluorescence intensities relative to the empty pCAG-EGxxFP vector by plate reader measurements. HEK293T cells were co-transfected with pCAG-EG_on-target_FP+sgRNA_X or pCAG-EG_non-target_FP+sgRNA_X. X=SNP-variant 749G (A), SNP-variant 749A (B), SNP-variant 756C (C) and SNP-variant 756T (D). sgRNAs marked by a number in a circle showed the desired effect of strong CRISPR/Cas9 activity on the pathologic allele while the wildtype allele remained uneffected. The reference to SEQ ID NO: 14 is to be replaced by a reference to SEQ ID NO: 54 and the reference to SEQ ID NO: 15 is to be replaced by a reference to SEQ ID NO: 55 as the data were generated by using sgRNAs according to SEQ ID NO: 54 and 55.

Figure 13:
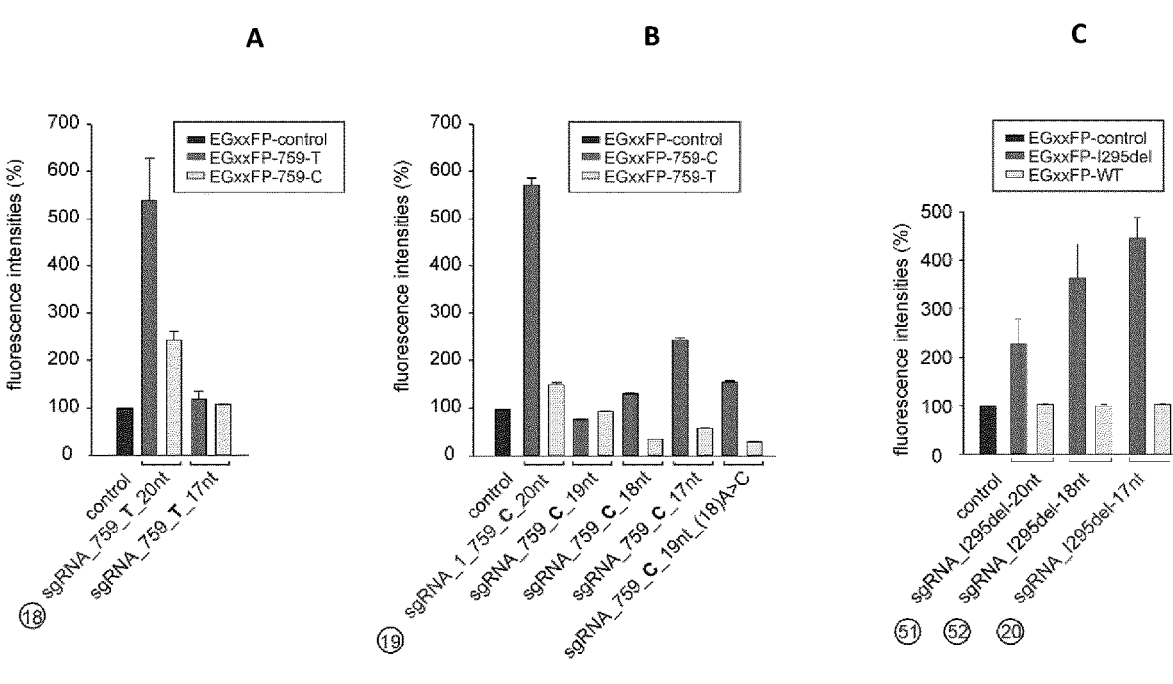

FIG. 13 shows the optimization of computationally designed sgRNAs. More specifically, the optimization of sgRNA specificity in HEK293T cells is shown. Quantification of EGFP fluorescence intensities relative to the empty pCAG-EGxxFP vector by plate reader measurements. HEK293T cells were transfected with pCAG-EG_on-target_FP+sgRNA_X or pCAG-EG_non-target_FP+sgRNA_X. X=SNP-variant 759T (A), SNP-variant 759C (B) and SNP-variant 1295del (C). sgRNAs marked by a number in a circle showed the desired effect of strong CRISPR/Cas9 activity on the pathologic allele while the wildtype allele remained uneffected.

The term "sgRNA molecule" as used herein refers to a single guide RNA molecule comprising crispr RNA (crRNA) and tracr RNA (tcRNA) in a single RNA molecule. crRNA is a sequence of usually 17 to 20 nucleotides which is complementary to the target DNA and may also be called the "targeting domain", "sgRNA sequence" or "sgRNA" in the present disclosure. The tcRNA is responsible for Cas9 endonuclease activity by serving as a binding scaffold for the Cas nuclease. An sgRNA molecule targets the complementary sequences of the target domain preferably by simple Watson and Crick base pairing. The crRNA and the tcRNA are preferably joined by a tetraloop which results in formation of an sgRNA molecule. Preferably, tcRNA are base pairs having a stem loop structure in itself and attaches to the endonuclease enzyme. The crRNA identifies the specific complementary target region which is cleaved by Cas9 after its binding with crRNA and tcRNA. With the modifications in the crRNA sequences of the sgRNA molecule, the binding location, efficiency and specificity can be changed.

The term "Cas9 molecule" as used herein refers to a molecule that encodes the CRISPR associated protein 9. The Cas9 protein plays a vital role in the immunological defense of certain bacteria against DNA viruses and plasmids. Its main function is to cut DNA and therefore it can alter a cell's genome. More particularly, Cas9 is an RNA-guided DNA endonuclease enzyme associated with the Clustered Regularly Interspaced Short Palindromic Repeats (shortly CRISPR) adaptive immune system in e.g. *Streptococcus pyogenes*. *S. pyogenes* utilizes CRISPR to memorize and Cas9 to later interrogate and cleave foreign DNA, such as invading bacteriophage DNA. Cas9 performs this interrogation by unwinding foreign DNA and checking for sites complementary to the spacer region of about 17 to 20 bp in the guide RNA. If the DNA substrate is complementary to the guide RNA, Cas9 cleaves the invading DNA. In molecular biology, Cas9 is used in the CRISPR/Cas9-mediated genome editing technology. The term "Cas9" may be used for naturally occurring Cas9 as e.g. SpCas9 or it may be used for recombinant Cas9 comprising one or more mutations in comparison to wildtype Cas9.

The term "SpCas9" as used herein refers to the Cas9 protein of *Streptococcus pyogenes*. It may be used for naturally occurring SpCas9 or for recombinant SpCas9 comprising one or more mutations in comparison to wildtype SpCas9.

The term "protospacer adjacent motif (PAM)" as used herein refers to a short sequence motif of preferably 2 to 6 base pairs following the target DNA sequence that is specific for each Cas subtype (e.g. PAM site 5'-NGG-3' for SpCas9). The absence of such a PAM sequence results in the inability of Cas9 to cleave the DNA target and is therefore the limiting factor in addressing a particular nucleotide sequence.

The term "self-limiting all-in-one AAV" as used herein refers to an adenovirus-associated virus where SpCas9 and sgRNA are engineered into a single AAV expression plasmid. The "all-in-one"-vector comprises preferably a truncated CMV minimal promoter sequence for SpCas9 expression and a truncated U6 minimal promoter sequence to drive expression of the sgRNA domain. In addition, SpCas9 self-limiting sequences are introduced into the AAV vector to suppress sustained Cas9 expression and unwanted off-target cleavage. Therefore, the targeting domain of the sgRNA molecule plus the corresponding PAM-site is added before and after the SpCas9 sequence. In this configuration, SpCas9 is guided for both, targeted genomic cleavage and cleavage of the AAV plasmid itself to delete the SpCas9 sequence and thereby limit the production of SpCas9 protein. Thus, a "self-limiting all-in-one AAV vector" comprises an SpCas9 sequence, an sgRNA molecule and self-limiting targeting domains of the sgRNA molecule plus the corresponding PAM-site.

The term "BEST1" as used herein is a shortcut for bestrophin-1. It can synonymously be used with the term "VMD2". BEST1 belongs to the bestrophin family of four evolutionary related genes (BEST1-4), that encode for integral membrane proteins. In humans, they function in particular as calcium-activated anion channels although each is specific in terms of gene regulation and tissue distribution of the protein.

The term "BEST1-related retinopathies" relates to retinopathies caused by mutations in the BEST1 gene (MIM 607854). BEST1 protein localizes most prominently to the basolateral plasma membrane of the RPE in the back of the eye. Mutations in the BEST1 gene affect BEST1 localization, protein stability and ion gating properties. As a consequence, these functional impairments result in loss of BEST1 channel function, in particular anion transport function, more preferably chloride transport function, which ultimately causes damage to the retina.

The term "Best macular dystrophy" as used herein may also be called "Best vitelliform macular dystrophy (BVMD)", "vitelliform macular dystrophy-2 (VMD2)", or short "Best disease". It is a hereditary retinal dystrophy involving the RPE/photoreceptor complex, characterized in early stages of the diseases by the appearance of yellow "egg-yolk"-like lesions in the macular area. It is the most common phenotype of the group of diseases of bestrophinopathies. Subjects suffering from any disease grouped within the bestrophinopathies, and as that specifically the autosomal dominant Best macular dystrophy, have a mutation in the BEST1 gene which leads to a loss of channel function and eventually retinal degeneration.

The term "autosomal dominant vitreoretinochoroidopathy (ADVIRC)" as used herein refers to a chorioretinal pigmentary disorder. According to the state of the art, in particular the five BEST1 gene mutations p. (Gly83Asp), p. (Val86Met), p. (Val235Ala), p. (Tyr236Cys), and p. (Val239Met) are causative for ADVIRC. The disease is classically characterized by a peripheral retinal circumferential hyperpigmented band with a well-defined posterior demarcation and can be associated with developmental ocular anomalies such as microcornea, microphthalmos, angle closure glaucoma, and cataract.

The term "restoring BEST1 channel function" particularly refers to a repair of the BEST1 anion transport function, in particular the chloride transport function, if the BEST1 channel function is impaired e.g. by one or more mutations in the BEST1 gene. The repair of BEST1 channel function can be determined in a given assay in CRISPR/Cas-treated patient-derived cell lines relative to the measurable level of BEST1 channel function in untreated cells, when tested under the same conditions and compared to BEST1 channel function of a control having no mutations in the BEST1 gene. The BEST1 channel function is restored according to the invention if at least about 10%, 20%, 30%, 40%, 50%, 60%, 70%, 80%, 90%, 95%, 98%, 99% or more of BEST1 channel function can be restored.

The term "pathologic allele" as used herein refers to the allele of the BEST1 gene carrying the mutation which results in the respective disease as e.g. the BEST1 related retinopathies described herein. In particular, the term "pathologic allele" as used herein refers to one of a pair of gene sequences or DNA sequences at a particular genomic location inherited from one parent. More particularly, said "pathologic allele" is responsible for the expression of the pathogenic mutant BEST1 gene transcript which leads to a loss of channel function and thus causing a BEST1-related retinopathy as described herein.

The term "wildtype BEST1 gene" as used herein preferably refers to a BEST1 gene encoding a functional BEST1 gene transcript, which ensures BEST1 anion transport function. Accordingly, a subject carrying two copies of a wildtype BEST1 allele is not suffering from a BEST1-related retinopathy as described herein.

The term "comprising" as used herein shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The object of the present invention is the provision of new means for treatment of autosomal dominant BEST1-related retinopathies by eliminating expression of the pathologic dominant-negative transcript using the CRISPR/Cas9-mediated genome editing technology to restore BEST1 channel function. This is in particular a possible therapeutic intervention in patients with Best macular dystrophy and ADVIRC. The present invention provides new means for editing of a target nucleic acid sequence in connection with autosomal dominant BEST1-related retinopathies.

In a first object of the present invention it is envisaged to provide an sgRNA molecule comprising a targeting domain, wherein said targeting domain comprises a sequence selected from the group consisting of SEQ ID NOs: 1-20 and 39 to 55. The targeting domain preferably binds to a target domain in the BEST1 gene. Preferably, the targeting domain has a length of 17 to 20 nucleotides. The sequences according to SEQ ID NOs: 1 to 20 and 39 to 55 have been identified to be highly efficient and specific for exclusively suppressing the pathologic BEST1 allele while leaving the wildtype allele intact and by showing no off-target effects in the genome. The targeting domain of the sgRNA molecule preferably corresponds to the crRNA of the sgRNA molecule. In addition to the targeting domain, the sgRNA molecule according to the present invention preferably comprises a tcRNA domain. In a preferred embodiment, the tcRNA domain of the sgRNA molecule comprises a nucleic acid sequence according to SEQ ID NO: 21.

The present invention further provides a sgRNA molecule comprising a targeting domain for specifically targeting a SNP in the BEST1 coding region of a pathologic allele, wherein said targeting domain consists of a sequence selected from the group consisting of SEQ ID NO: 3-8, 41-44, 14-20 and 50-55.

The present invention further provides a sgRNA molecule combination of two sgRNA molecules, i.e. a first sgRNA molecule and a second sgRNA, each comprising a targeting domain for specifically targeting a SNP in the BEST1 gene coding region of a pathologic allele or for specifically targeting a SNP in the BEST1 gene non-coding region of a pathologic allele, wherein (i) if the targeting domain of the first sgRNA consists of a sequence according to SEQ ID NO: 20 or 51-52, the targeting domains of the second sgRNA consists of a sequence according to SEQ ID NO: 1-19, 39-50 or 53-55;

(ii) if the targeting domain of the first sgRNA consists of a sequence according to SEQ ID NO: 1-2 or 39-40, the targeting domains of the second sgRNA consists of a sequence according to SEQ ID NO: 3-20 or 41-55;

(iii) if the targeting domain of the first sgRNA consists of a sequence according to SEQ ID NO: 3-6 or 41, the targeting domains of the second sgRNA consists of a sequence according to SEQ ID NO: 1-2, 39-40, 7-20 or 42-55;

(iv) if the targeting domain of the first sgRNA consists of a sequence according to SEQ ID NO: 7-8 or 42-44, the targeting domains of the second sgRNA consists of a sequence according to SEQ ID NO: 1-6, 39-41, 9-20 or 45-55;

(v) if the targeting domain of the first sgRNA consists of a sequence according to SEQ ID NO: 9-10, 45-46 or 53, the targeting domains of the second sgRNA consists of a sequence according to SEQ ID NO: 1-8, 39-44, 11-20, 47-52 or 54-55;

(vi) if the targeting domain of the first sgRNA consists of a sequence according to SEQ ID NO: 11-12 or 47-48, the targeting domains of the second sgRNA consists of a sequence according to SEQ ID NO: 1-10, 39-46, 13-20 or 49-55;

(vii) if the targeting domain of the first sgRNA consists of a sequence according to SEQ ID NO: 13 or 49, the targeting domains of the second sgRNA consists of a sequence according to SEQ ID NO: 1-12, 39-48, 14-20 or 50-55;

(viii) if the targeting domain of the first sgRNA consists of a sequence according to SEQ ID NO: 14-15 or 54-55, the targeting domains of the second sgRNA consists of a sequence according to SEQ ID NO: 1-13, 39-53 or 16-20;

(ix) if the targeting domain of the first sgRNA consists of a sequence according to SEQ ID NO: 16-17 or 50, the targeting domains of the second sgRNA consists of a sequence according to SEQ ID NO: 1-15, 39-49, 18-20 or 51-55; or (x) if the targeting domain of the first sgRNA consists of a sequence according to SEQ ID NO: 18-19, the targeting domains of the second sgRNA consists of a sequence according to SEQ ID NO: 1-17, 39-55, or 20.

Thus, preferred combinations are SEQ ID NO: 1 with any one of SEQ ID NO: 3-20 or 41-55; SEQ ID NO:2 with any one of SEQ ID NO: 3-20 or 41-55; SEQ ID NO: 39 with any one of SEQ ID NO: 3-20 or 41-55; SEQ ID NO: 40 with any one of SEQ ID NO: 3-20 or 41-55; SEQ ID NO: 3 with any one of SEQ ID NO: 1-2, 39-40, 7-20 or 42-55; SEQ ID NO: 4 with any one of SEQ ID NO: 1-2, 39-40, 7-20 or 42-55; SEQ ID NO: 5 with any one of SEQ ID NO: 1-2, 39-40, 7-20 or 42-55; SEQ ID NO: 6 with any one of SEQ ID NO: 1-2, 39-40, 7-20 or 42-55; SEQ ID NO: 41 with any one of SEQ ID NO: 1-2, 39-40, 7-20 or 42-55; SEQ ID NO: 7 with any one of SEQ ID NO: 1-6, 39-41, 9-20 or 45-55; SEQ ID NO: 8 with any one of SEQ ID NO: 1-6, 39-41, 9-20 or 45-55; SEQ ID NO: 42 with any one of SEQ ID NO: 1-6, 39-41, 9-20 or 45-55; SEQ ID NO: 43 with any one of SEQ ID NO: 1-6, 39-41, 9-20 or 45-55; SEQ ID NO: 44 with any one of SEQ ID NO: 1-6, 39-41, 9-20 or 45-55; SEQ ID NO: 9 with any one of SEQ ID NO: 1-8, 39-44, 11-20, 47-52, or 54-55; SEQ ID NO: 10 with any one of SEQ ID NO: 1-8, 39-44, 11-20, 47-52, or 54-55; SEQ ID NO: 45 with any one of SEQ ID NO: 1-8, 39-44, 11-20, 47-52, or 54-55; SEQ ID NO: 46 with any one of SEQ ID NO: 1-8, 39-44, 11-20, 47-52, or 54-55; SEQ ID NO: 53 with any one of SEQ ID NO: 1-8, 39-44, 11-20, 47-52 or 54-55; SEQ ID NO: 11 with any one of SEQ ID NO: 1-10, 39-46, 13-20 or 49-55; SEQ ID NO: 12 with any one of SEQ ID NO: 1-10, 39-46, 13-20 or 49-55; SEQ ID NO: 47 with any one of SEQ ID NO: 1-10, 39-46, 13-20 or 49-55; SEQ ID NO: 48 with any one of SEQ ID NO: 1-10, 39-46, 13-20 or 49-55; SEQ ID NO: 13 with any one of SEQ ID NO: 1-12, 39-48, 14-20 or 50-55; SEQ ID NO: 49 with any one of SEQ ID NO: 1-12, 39-48, 14-20 or 50-55; SEQ ID NO: 14 with any one of SEQ ID NO: 1-13, 39-53 or 16-20; SEQ ID NO: 15 with any one of SEQ ID NO: 1-13, 39-53 or 16-20; SEQ ID NO: 54 with any one of SEQ ID NO: 1-13, 39-53 or 16-20; SEQ ID NO: 55 with any one of SEQ ID NO: 1-13, 39-53 or 16-20; SEQ ID NO: 16 with any one of SEQ ID NO: 1-15, 39-49, 18-20 or 51-55; SEQ ID NO: 17 with any one of SEQ ID NO: 1-15, 39-49, 18-20 or 51-55; SEQ ID NO: 50 with any one of SEQ ID NO: 1-15, 39-49, 18-20 or 51-55; SEQ ID NO: 18 with any one of SEQ ID NO: 1-17, 39-55, or 20; SEQ ID NO: 19 with any one of SEQ ID NO: 1-17, 39-55, or 20; SEQ ID NO: 20 with any one of SEQ ID NO: 1-19, 39-50 or 53-55; SEQ ID NO: 51 with any one of SEQ ID NO: 1-19, 39-50 or 53-44; SEQ ID NO: 52 with any one of SEQ ID NO: 1-19, 39-50 or 53-55.

Specifically targeting a SNP in the BEST1 gene of a pathologic allele means that specifically only the pathologic allele is targeted by the sgRNAs or sgRNA combinations of the present invention. Consequently, the wildtype allele remains unaffected by the approach of the present invention. If the present invention refers only to a single sgRNA molecule, said single sgRNA targets a SNP in the BEST1 gene coding region (exonic sequence). If the present invention refers to a sgRNA molecule combination of two sgRNA molecules, both sgRNA molecules may target a SNP in the BEST1 gene coding region (exonic sequence) or both sgRNA molecules may target a SNP in the BEST1 gene non-coding region (intronic sequence). Alternatively, the first sgRNA molecule of said combination may target a SNP in the BEST1 gene non-coding region and the second sgRNA molecule of said combination may target a SNP in the BEST1 coding region or the first sgRNA molecule may target a SNP in the BEST1 gene coding region and the second sgRNA molecule may target a SNP in the BEST1 non-coding region. The present invention, therefore, provides a highly allele-specific approach by explicitly excluding the use of sgRNAs which induce double strand breaks within the BEST1 genomic region with unknown consequences for the expression of BEST1 or other genes in cis or trans position.

In a preferred embodiment, the sgRNA molecule combination are as follows:

(xi) if the targeting domain of the first sgRNA consists of a sequence according to SEQ ID NO: 1 or 39, the targeting domains of the second sgRNA consists of a sequence according to SEQ ID NO: 13 or 49;

(xii) if the targeting domain of the first sgRNA consists of a sequence according to SEQ ID NO: 9 or 45, the targeting domains of the second sgRNA consists of a sequence according to SEQ ID NO: 11, 47, 13 or 49;

(xiii) if the targeting domain of the first sgRNA consists of a sequence according to SEQ ID NO: 11 or 47, the targeting domains of the second sgRNA consists of a sequence according to SEQ ID NO: 13 or 49;

(xiv) if the targeting domain of the first sgRNA consists of a sequence according to SEQ ID NO: 10, 46 or 53, the targeting domains of the second sgRNA consists of a sequence according to SEQ ID NO: 12 or 48; or (xv) if the targeting domain of the first sgRNA consists of a sequence according to SEQ ID NO: 13, the targeting domains of the second sgRNA consists of a sequence according to SEQ ID NO: 15 or 55.

In a further preferred embodiment, the present invention refers to those sgRNA molecules, wherein the targeting domain has a length of 17, 18 or 19 nucleotides i.e. according to SEQ ID NO: 3-4, 6-8, 16-17, 20, 40, 42, 50 and 52. In a further preferred embodiment, the present invention refers to sgRNA molecule combination, wherein the targeting domain of the first and second sgRNA molecule has a length of 17, 18 or 19 nucleotides i.e. any of the combinations disclosed herein but lacking combinations with SEQ ID NO: 39, 41, 43, 44, 45, 46, 47, 48, 49, 14, 15, 18, 19, 51, 54 and 55. The advantage of sgRNA molecules having a target domain as short as possible is the reduction of genome-wide off-targets as sequence binding by a non-complementary base in a short sgRNA is energetically more destabilised than in a long sgRNA. In the short sgRNA, the deviating base has a stronger energetic weighting, since fewer complementary bases can contribute to the stability of the binding. Hence, truncated sgRNA molecules may lower is the risk of genome-wide off-target. However, with a decreasing length of the targeting domain also the efficacy and specificity of a targeting domain might decrease.

Accordingly, the most effective targeting domains for addressing specific SNPs are not predictable but have to be designed individually.

The present invention further relates to a nucleic acid comprising an sgRNA domain according to the present invention. The sgRNA domain according to the present invention consists of a sequence that encodes the sgRNA molecule according to the present invention. Thus, the present invention further relates to a nucleic acid comprising a sequence that encodes the sgRNA molecule according to the present invention. The present invention further relates to a nucleic acid comprising a combination of two sgRNA domains, wherein the first sgRNA domain consists of a sequence that encodes the first sgRNA molecule of any sgRNA molecule combination described herein and the second sgRNA domain consists of a sequence that encodes the second sgRNA molecule of the selected sgRNA molecule combination.

The present invention further relates to a nucleic acid combination of two nucleic acids, wherein (i) the first nucleic acid comprises a sgRNA domain consisting of a sequence that encodes the first sgRNA molecule of any sgRNA molecule combination according to the present invention, and (ii) the second nucleic acid comprises a sgRNA domain consisting of a sequence that encodes the second sgRNA molecule of the selected sgRNA molecule combination according to the present invention.

The nucleic acid according to the present invention further comprises preferably a sequence encoding a Cas9 molecule, more preferably a SpCas9 molecule. Of a nucleic acid combination according to the present invention one or both nucleic acids may further comprise a sequence encoding a Cas9 molecule, in particular a SpCas9 molecule. In a preferred embodiment, the nucleic acid according to the present invention comprising a combination of two sgRNA domains does not further comprises a sequence encoding a Cas9 molecule.

The in vivo translation of the genome editing tools provided by the present invention requires the efficient delivery of the Cas9/sgRNA machinery into post-mitotic RPE cells in vivo. This can for example be realized by the use of suitable viruses such as recombinant adenovirus-associated viruses (AAV).

A further aspect of the present invention provides therefore a recombinant AAV comprising a nucleic acid according to the present invention. Preferably, the recombinant AAV comprises both one sgRNA domain and a sequence encoding a Cas9 molecule, in particular a SpCas9 molecule. The gene encoding SpCas9 has preferably a size of about 4.0 to about 4.2 kb, more preferably of about 4.1 kb. In a preferred embodiment SpCas9 comprises an amino acid sequence as shown in SEQ ID NO: 22. In a further preferred embodiment SpCas9 is encoded by a nucleic acid sequence as shown in SEQ ID NO: 23.

A further aspect of the present invention provides a recombinant adenovirus-associated virus (AAV) comprising the nucleic acid comprising a combination of two sgRNA domains or a nucleic acid combination according to the present invention. In this case, the sequences for expressing Cas9, in particular SpCas9, are preferably provided in a second recombinant AAV, preferably not comprising any sgRNA domains.

In still a further aspect, the present invention provides a recombinant adenovirus-associated virus (AAV) combination of two recombinant adenovirus-associated virus (AAV), wherein (i) the first recombinant adenovirus-associated virus (AAV) comprises the first nucleic acid of any nucleic acid combination according to the present invention, and (ii) the second recombinant adenovirus-associated virus (AAV) comprises the second nucleic acid of the selected nucleic acid combination.

The recombinant AAV according to the present invention can be designed for combination with a second recombinant AVV as e.g. shown in FIG. 9A, wherein the domain "1295del" refers to a specific sgRNA targeting domain which can be replaced by any of the sgRNA targeting domains according to the present invention as long as they are replaced in one set of associated AVVs by the same targeting domain. In particular, in such a dual vector system a full-length RSV promoter for SpCas9 expression may be used in the first vector and a strong full-length U6 promoter for expression of the sgRNA domain in the second vector.

According to a highly preferred embodiment of the present invention, the recombinant AVV comprising the nucleic acid comprising one sgRNA domain (either of a sgRNA molecule according to the present invention or of a first or second sgRNA domain of a sgRNA molecule combination) is an "all-in-one" AAV vector comprising a minimal CMV promoter sequence for Cas9, in particular SpCas9, expression. The minimal CMV promoter sequence is preferably a fragment of a full length CMV promoter, in particular one continuous fragment of a full length CMV promoter. Preferably, it is a fragment of the full length CMV promoter as shown in SEQ ID NO: 24. The fragment of the full length CMV promoter has preferably a length of about 90 bp to about 180 bp, more preferably of about 100 bp to about 159 bp. Especially preferred is a minimal CMV promoter of 100 bp comprising a sequence as shown in SEQ ID NO: 25. Most preferred is a minimal CMV promoter of 159 bp comprising a sequence as shown in SEQ ID NO: 26.

Additionally, the "all-in-one" AVV comprises preferably a promoter for driving expression of the sgRNA domain in combination with a poly A signal sequence. An example for a suitable promoter for driving expression of the sgRNA domain is a minimal H1 promoter sequence. The minimal H1 promoter sequence is preferably a fragment of a full length H1 promoter, in particular one continuous fragment of a full length H1 promoter. Preferably, it is a fragment of the full length H1 promoter as shown in SEQ ID NO: 27. The fragment of the full length H1 promoter has preferably a length of about 80 bp to about 120 bp, more preferably of about 90 bp to about 100 bp, most preferably of about 95 bp. Especially preferred is a minimal H1 promoter of 95 bp comprising a sequence as shown in SEQ ID NO: 28.

In a highly preferred embodiment of the present invention, the promoter for driving expression of the sgRNA domain is a shortened U6 promoter. The shortened U6 promoter sequence is preferably a fragment of a full length U6 promoter. It may be one continuous fragment of a full length U6 promoter or a fragment of a full length U6 promoter consisting of two continuous fragments of a full length U6 promoter. If the fragment consists of two continuous fragments of a full length U6 promoter it comprises preferably the 5' and the 3' end of the full length U6 promoter, i.e. it comprises a deletion of nucleic acids within the full length U6 promoter sequence. Said deletion has preferably a length of about 130 to about 150 bp, more preferably of about 142 bp. Preferably, the shortened U6 promoter is a fragment of the full length U6 promoter as shown in SEQ ID NO: 29. The fragment of the full length U6 promoter has preferably a length of about 80 bp to about 120 bp, more preferably of about 90 bp to about 110 bp, most preferably of about 99 bp. Especially preferred is a shortened U6 promoter of 99 bp comprising a sequence as shown in SEQ ID NO: 30.

The poly A signal sequence is preferably a minimal poly A signal sequence which is a fragment of a full poly A signal sequence. The fragment of the full-length poly A signal sequence has preferably a length of about 30 bp to about 60 bp, more preferably of about 40 bp to about 55 bp, most preferably of about 49 bp. Especially preferred is a minimal poly A signal sequence of 49 bp comprising a sequence as shown in SEQ ID NO: 31.

In a preferred embodiment the above listed domains of the recombinant AAV are arranged as shown in FIG. 9B.

In a particularly preferred embodiment, the present invention provides a self-limiting "all-in-one" AAV vector comprising:

(i) a shortened U6 promoter sequence for promoting expression of the sgRNA domain, preferably according to SEQ ID NO: 30, wherein the shortened U6 promoter is located upstream of the sgRNA domain;

(ii) a minimal CMV promoter sequence, preferably according to SEQ ID NO: 26, for promoting SpCas9 expression, wherein the CMV promoter sequence is located upstream of the sequence encoding the SpCas9 molecule; and (iii) a first and a second self-limiting sequence each comprising the targeting domain of the sgRNA molecule flanked by a PAM site sequence at its 3' end, wherein the first self-limiting sequence is located 5' of the SpCas9 sequence and the second self-limiting sequence is located 3' of the SpCas9 sequence.

The sequence that codes for the PAM site has preferably a length of 3, 4, 5, or 6 nucleotides depending on the bacterial species expressing the Cas endonuclease. In a further preferred embodiment, the PAM sequence comprises the amino acid sequence "NGG" or "NAG". In a further preferred embodiment, the sgRNA targeting domain according to SEQ ID NO: 1, 2, 5, 6, 7, 9, 10, 11, 12, 13, 14, 54, 15, 55, 16, 17, 18, 19, 20, 39, 40, 42, 43, 45, 53, 46, 47, 48, 49, 50, 51 and 52 is combined with a PAM comprising the amino acid sequences "NGG", the sgRNA targeting domain according to SEQ ID NO: 3, 41, 4, 8 and 44 is combined with a PAM comprising the amino acid sequences "NAG".

The self-limiting "all-in-one" AAV vector according to the present invention as described above does not comprise any full length U6 promoter sequences or full length CMV promoter sequences.

In a further preferred embodiment, the present invention refers to a recombinant AAV as shown in FIG. 9B. In FIG. 9B the domains "1295del" refers to a specific sgRNA targeting domain (flanked by a PAM sequence), which can be replaced by any of the sgRNA targeting domains according to the present invention as long as they are replaced in the all-in-one AAV by the same targeting domain. The term "1295del sgRNA" in FIG. 9B refers to an sgRNA domain (i.e. a complete sgRNA) comprising the specific sgRNA targeting domain "1295del". The domain "1295del sgRNA" can be replaced by any of the sgRNA domains according to the present invention as long as it is replaced in accordance with the replacement of the sgRNA targeting domains 5' and 3' of the SpCas9 sequence.

In a preferred embodiment of the present invention, the recombinant AAV comprises an AAV2-ITR sequence, a shortened U6 promoter sequence, preferably according to SEQ ID NO: 30, an sgRNA domain according to the present invention, a CMV promoter sequence for promoting SpCas9 expression, preferably according to SEQ ID NO: 26, a first sgRNA targeting domain which is (i) identical to the sgRNA targeting domain of the chosen sgRNA domain and (ii) flanked by a PAM site sequence, a SpCas9 sequence, preferably according to SEQ ID NO: 23, a second sgRNA targeting domain which is (i) identical to the sgRNA targeting domain of the chosen sgRNA domain and (ii) flanked by a PAM site sequence and an AVV2-ITR sequence. Preferably, the order of the listed domains corresponds to the order of the domains in the AAV in 5' to 3' direction. In a particularly preferred embodiment the sgRNA targeting domain comprises a sequence as shown in SEQ ID NOs: 1 to 20, or 39-55.

Preferably, the all-in-one recombinant AAV according to the present invention has a length of about 4.5 to about 4.9 kb, more preferably of about 4.6 to about 4.8 kb.

Of the adenovirus-associated virus (AAV) combination according to the present invention one or both AAVs of the combination may be an "all-in-one" AAV vector or a self-limiting "all-in-one" AAV vector as described herein.

The present invention also refers to the sgRNA molecule according to any of the embodiments outlined above, the sgRNA molecule combination according to any of the embodiments outlined above, the nucleic acid according to any of the embodiments outlined above (i.e. including embodiments of the nucleic acid comprising one sgRNA and embodiments of the nucleic acid comprising a sgRNA combination), the nucleic acid combination according to any of the embodiments outlined above, the recombinant AAV according to any of the embodiments outlined above (i.e. including embodiments of the AAV comprising one sgRNA embodiments of the AVV comprising a sgRNA combination), or the recombinant AAV combination according to any of the embodiments outlined above for use in a method for treatment of the human or animal body by surgery or therapy.

Moreover, the present invention refers to the sgRNA molecule according to any of the embodiments outlined above, the sgRNA molecule combination according to any of the embodiments outlined above, the nucleic acid according to any of the embodiments outlined above, the nucleic acid combination according to any of the embodiments outlined above, the recombinant AAV according to any of the embodiments outlined above, or the recombinant AAV combination according to any of the embodiments outlined above for use in method of treating or preventing BEST1-related retinopathies, in particular autosomal dominant BEST1-related retinopathies, preferably selected from the group consisting of Best macular dystrophy and ADVIRC.

The subject to be treated is preferably a human or an animal, in particular a mammal, most preferably a human.

In a preferred embodiment the autosomal dominant BEST1-related retinopathies which can be treated by the teaching provided by the present invention is a disease where heterozygous dominant mutations act through a gain of function or operate in a dominant negative mode.

Preventing autosomal dominant BEST1-related retinopathies comprises preferably delaying the onset and/or progression of BEST1-related retinopathies.

The method of treating, preventing and/or delaying the onset or progression of autosomal dominant BEST1-related retinopathies preferably comprises the administration of a sgRNA molecule, a sgRNA molecule combination, a nucleic acid, a nucleic acid combination, a recombinant AAV, or a recombinant AAV combination according to any of the embodiments of the present invention to the subject. Preferably, the sgRNA molecule, sgRNA molecule combination, the nucleic acid, nucleic acid combination, the recombinant AAV, or recombinant AAV combination is administered in an amount sufficient to improve chloride conductance across the basolateral membrane of the RPE of the subject. It is preferably administered in an amount sufficient to restore BEST1 channel function. The restoration of BEST1 channel function is preferably realized by eliminating or decreasing the expression of the pathologic dominant-negative BEST1 gene transcript with CRISPR/Cas9-mediated genome editing technology while the expression of the wildtype BEST1 gene transcript is maintained For doing this, the sgRNA molecule, the sgRNA molecule combination, the nucleic acid, the nucleic acid combination, the recombinant AAV, or the recombinant AAV combination is preferably delivered into post mitotic RPE cells in vivo.

In an especially preferred embodiment, the method comprises the steps of (i) evaluating the subject's vision before treatment;

(ii) determining the disease-associated mutation and common known SNPs across the individual genomic BEST1 locus to define both haplotypes for the subject;

(iii) administering the sgRNA molecule, the sgRNA molecule combination, the nucleic acid, the nucleic acid combination, the recombinant AAV or the recombinant AAV combination according to the present invention to the subject; and (iv) evaluating of subject's vision after step (iii).

Step (ii) may be performed by obtaining a blood sample of the subject and extracting and analysing its DNA.

Molecular genetic testing of the BEST1 gene and analysis of the BEST1 haplotype tagging SNPs can then be performed from the extracted peripheral blood DNA. Mutation and SNP analysis may be done by the Sanger dideoxy chain termination method, a technique for DNA sequencing based upon the selective incorporation of chain-terminating dideoxynucleotides (ddNTPs) by DNA polymerase during in vitro DNA replication. Specifically, the nucleotide sequence of the (i) 11 coding sequences (exons) and the respective flanking intronic regions (about 20 base pairs each) and (ii) of the identified 22 SNPs (FIGS. 3 and 4) will be sequenced from the BEST1 gene and flanking genomic BEST1 region of the subject.

In a preferred embodiment, step (iii) is performed by subretinal, intravitreal or suprachoroidal injection of recombinant AAV particles according to the present invention.

The present invention also refers to a pharmaceutical composition comprising an sgRNA molecule, a sg RNA molecule combination, a nucleic acid, a nucleic acid combination, a recombinant AAV, or a recombinant AAV combination according to the present invention and a pharmaceutical acceptable excipient and/or carrier. The present invention also refers to a combination of pharmaceutical combinations, wherein the first pharmaceutical combination comprises the first component of any of the combinations according to the present invention and the second pharmaceutical combination comprises the second component of the selected combination according to the present invention. Moreover, the present invention refers to a pharmaceutical composition or combination of pharmaceutical compositions according to the present invention for use in a method for treatment of the human or animal body by surgery or therapy. Additionally, the present invention refers to a pharmaceutical composition or combination of pharmaceutical compositions according to the present invention for use in method of treating or preventing autosomal dominant BEST1-related retinopathies, in particular selected from the group consisting of Best macular dystrophy and ADVIRC.

The pharmaceutical composition or the combination of pharmaceutical compositions according to the present invention may additionally contain one or more conventional additive(s).

The sgRNA molecule, the sg RNA molecule combination, the nucleic acid, the nucleic acid combination, the recombinant AAV, the recombinant AAV combination the pharmaceutical composition, or the combination of pharmaceutical compositions according to the present invention is preferably formulated for subretinal, intravitreal or suprachoroidal injection.

The sgRNA molecule, the sgRNA molecule combination, the nucleic acid, the nucleic acid combination, the recombinant AAV, or the recombinant AAV combination the pharmaceutical composition, or the combination of pharmaceutical compositions according to the present invention may be administered to the subject in need thereof in an effective amount. The effective amount of the compound to be administered can be readily determined by those skilled in the art during pre-clinical trials and clinical trials by methods familiar to physicians and clinicians. The preferred route of administration is a subretinal, intravitreal or suprachoroidal injection.

The administration of the single components of any of the combinations according to the present invention is preferably performed simultaneously. They may be administered in the same pharmaceutical formulation.

In another aspect the present invention relates to a process of preparation of a pharmaceutical composition, said process comprising admixing sgRNA molecules, sgRNA molecule combinations, nucleic acids, nucleic acid combinations, recombinant AAVs or recombinant AAV combinations according to the present invention with a pharmaceutically acceptable diluent, excipient or carrier.

The present invention also relates to a pharmaceutical pack comprising one or more compartments, wherein at least one compartment comprises sgRNA molecules, each first and a second sgRNA molecules of any of the sgRNA combinations, nucleic acids, each first and second nucleic acids of any of the nucleic acid combinations, recombinant AAVs, or each first and second recombinant AAVs of any of the recombinant AAV combinations according to the present invention, the pharmaceutical composition or each first and second pharmaceutical composition of any of the pharmaceutical compositions combinations of the present invention. The first and second component of the combinations according to the present invention may be comprised in the same compartment or in two separate compartments of the pharmaceutical pack.

In a specific embodiment of the present invention the sgRNA molecule, the sgRNA molecule combination, the nucleic acid, the nucleic acid combination, the recombinant AAV, the recombinant AAV combination, the pharmaceutical composition and/or the pharmaceutical composition combination according to the present invention is used as a medicament, in particular for the treatment of autosomal dominant BEST1-related retinopathies, in particular selected from the group consisting of Best macular dystrophy and ADVIRC.

In another specific embodiment of the present invention the sgRNA molecule, the sgRNA molecule combination, the nucleic acid, the nucleic acid combination, the recombinant AAV, the recombinant AAV combination, the pharmaceutical composition and/or the pharmaceutical composition combination according to the present invention is used in the manufacture of a medicament, in particular for the treatment of autosomal dominant BEST1-related retinopathies, in particular selected from the group consisting of Best macular dystrophy and ADVIRC.

A further aspect of the present invention is a method of treating autosomal dominant BEST1-related retinopathies, in particular selected from the group consisting of Best macular dystrophy and ADVIRC by administering or applying a sgRNA molecule, a sgRNA molecule combination, a nucleic acid, a nucleic acid combination, a recombinant AAV, a recombinant AAV combination, a pharmaceutical composition and/or or a pharmaceutical composition combination according to the present invention to a subject, in particular to a human or animal.

In yet a further aspect, the invention provides a method of restoring BEST1 channel function by editing of the target domain in the BEST1 gene, preferably by improving chloride conductance across the basolateral membrane of the RPE in a subject in need thereof. This is preferably done by CRISPR/Cas9-based gene editing by utilizing an sgRNA molecule, a sgRNA molecule combination, a nucleic acid, a nucleic acid combination, a recombinant AAV or a recombinant AAV combination according to the present invention. In particular, the gene editing using CRISPR/Cas9-mediated methods results in the suppression of pathogenic mutant BEST1 expression. Preferably, CRISPR/Cas9-mediated methods further results in that the expression of wildtype BEST1 is maintained. The method comprises administering to the subject an effective amount of sgRNA molecules, a combination of sgRNA molecules, nucleic acids, a combination of nucleic acids, recombinant AAVs, a combination of recombinant AAVs, a pharmaceutical composition and/or a combination of pharmaceutical compositions according to the present invention.

The following examples explain the present invention but are not considered to be limiting. It should be understood that the detailed description and specific examples disclosed herein, indicating particular embodiments of the invention, are given by way of illustration only, since various changes and modifications within the spirit and scope of the invention will become apparent to those skilled in the art from this description.

Example 1-In Silico SNP Analysis Based on Data from the 1000 Genome Project (1000G)

SNP heterozygosity in the European population across the BEST1 locus plus a 15 kb flanking region at the 5' end was analyzed by genotype imputation based on SNP data released from the 1000 Genomes Project (UCSC Genome Browser on Human February 2009 (GRCh37/hg19)). The dataset contains 502 individuals from the European population. To filter for SNPs in repetitive regions and low complexity DNA sequences the software RepeatMasker was used. Haplotype frequencies were estimated by the Hapview software.

Example 2-Generation of Cell Lines from Patients with Best Macular Dystrophy And Sanger Sequencing Analysis Skin biopsies were collected from 13 participants including 2 healthy controls and 11 patients carrying known BEST1 mutations in patients with Best macular dystrophy (N11K, S108R, R218C, Q238R, A243V and 1295del) and ADVIRC (V86M). Adult human dermal fibroblasts were established and reprogrammed into human induced pluripotent stem cells (hiPSCs) via overexpression of transcription factors OCT3/4, Sox2, Klf4 and c-Myc (Takahashi et al., 2007). The cells were subsequently differentiated into hiPSC-derived RPE cells as described by Brandl et al. (2014). Genotyping was carried out with genomic DNA extracted from patient and control fibroblasts and from blood samples of three affected family members by Sanger sequencing.

Example 3-Computational Design and Evaluation of Targeting sgRNAs

To computationally predict high quality sgRNA sequences two prediction programs were used, the "Optimised CRISPR Design Tool" (http://tools.genome-engineering.org) provided by the Zhang lab (MIT Broad Institute, Cambridge, USA) and "benchling" (http://benchling.com) which is provided by the company Benchling, San Francisco, USA Efficacy and allele specificity of sgRNAs were validated in vitro by a fluorescence-based assay in HEK293T cells (Mashiko et al., 2013). A 250-500 bp genomic fragment containing either the wild-type-(non-target) or mutation-associated (on-target) BEST1 sequence was cloned between the 5' and 3' EGFP fragments of the pCAG-EGxxFP plasmid. For expression of Cas9 and sgRNA, pX330 plasmids (Addgene, UK) were used. The pCAG-EGxxFP-target and pX330-sgRNA/Cas9 plasmid were co-transfected into HEK293T cells and the reconstituted EGFP fluorescence was measured 72 h after transfection on a plate reader.

Example 4-Genome Editing in hiPSCs and hiPSC-RPEs

Delivery of purified Cas9 protein/sgRNA ribonucleoprotein (RNP) complexes into hiPSCs and hiPSC-RPEs was performed through electroporation using the Amaxa Nucleofector Technology. Full length sgRNA was generated with the GeneArt Precision gRNA Synthesis Kit (Thermofisher Scientific, USA) which uses two single-stranded oligonucleotides coding for the target sequence and a complementary T7 promoter sequence. The pooled oligonucleotides are then PCR amplified, generating the sgRNA template for in vitro transcription. After purification the resulting sgRNA is complexed with recombinant GeneArt TrueCut *Streptococcus* Cas9 (SpCas9) Nuclease to form a stable RNP complex.

Example 5-Determination of Cleavage Efficiency and Specificity in Treated hiPSCs and hiPSC-RPEs To analyze editing efficiency in hiPSCs after transfection, the percentage of indel formation at the BEST1 target locus was determined by PCR amplification of extracted genomic DNA using primer pairs encompassing the target region. The PCR products were subcloned into the PCR-vector pGEM-T and 40-50 single clones were analyzed by Sanger sequencing.

Example 6-Generation of Patient hiPSC-RPE Cell Lines from CRISPR-Cas9-Treated Clonal Cells Single cell populations were generated by dissociating edited hiPSCs in 96-well plates. Clonal cells were expanded to generate duplicate plates for indel screening in the BEST1 on-target regions. Single clones from patient hiPSCs with confirmed double-strand breaks leading to frameshift mutations and premature stop codons were selected for differentiation into hiPSC-RPE cells for further characterization. A detailed procedure has been described previously (Brandl et al., 2014).

Example 7-Protein Sample Preparation, SDS Page, Quantitative Western Blot Analysis Whole cell protein sample preparation was performed as previously described in Milenkovic et al. (2015). Protein samples were separated by SDS-polyacrylamide gel electrophoresis on 10% gels and subsequently transferred onto Immobilon-FL (LI-COR Bioscience, Bad Homburg, Germany) membrane (Millipore, Bedford, MA, USA). Incubation of primary and secondary antibodies was carried out at 4° C. ON, respectively. Protein labeling was visualized by fluorescence detection using the Odyssey Fc Imaging System and signal intensities were quantified with the Image Studio software and normalized against beta-actin from the same blot.

Example 8-Immunofluorescence Labeling

Cell monolayers grown on transwell filters for 6 weeks were fixed in 4% paraformaldehyde (PFA)/PBS for 10 minutes and blocked by PBS containing 0.3% Triton X-100 and 10% goat serum for 25 min. Incubation with primary antibody against BEST1 and fluorescent-conjugated secondary antibody was performed at 4° C. ON. Immunolabelled hiPSC-RPE cells were imaged on a Zeiss confocal microscope LSM 510 (Zeiss, Göttingen, Germany).

Example 9-YFP-Halide Transport Assay

Human hiPSC-RPE cells were transduced by lentivirus particles which were produced by co-transfecting HEK293T cells with the yellow fluorescence protein (YFPH148Q/1152L)-pLJM1 and helper plasmids pMD2.G and psPAX2 using the Ca2+phospate transfection method. After six weeks of cultivation in 96-well black microtiter plates, cells were incubated with 70 mM iodide (I–) containing solution and basal YFP fluorescence was measured in a Tecan microplate reader. Subsequently I– was replaced with equal volume of Cl– containing solution and increase of YFP intensity was monitored for another 6 min in 60 sec intervals.

Example 10-Cloning Strategy for AAV Transfer Plasmids

The 95 bp truncated H1 promoter fragment was PCR amplified from vector pUC18-H1 RNAi (#87355, Addgene, UK). For the generation of the 99 bp U6 promoter two fragments (29 bp of the 5' end and 70 bp of the 3 end) of the full-length U6 promoter (241 bp) were PCR amplified from vector pAAV_U6_sgRNA_CMV_GFP (#85451, Addgene, UK) and ligated using the Gibson assembly cloning method (New England Biolabs, Germany). The sgRNA scaffold was amplified from the same vector and ligated with the shortened H1 and U6 fragments respectively. The 1295del 17nt sequence was ligated into the sgRNA scaffold by BbsI restriction cloning. Truncated CMV promoters (100 and 150 bp) were PCR amplified from the 3' end of the full-length CMV promoter of the pCDNA3 vector (Thermo Fisher Scientific, USA) and the resulting fragments then replaced the RSV promoter of vector pAAV_RSV_SpCas9 (=pAAV_159_SpCasp and pAAV_100_SpCas9) by restriction cloning. The shortened H1/sgRNA scaffold and U6/scaffold fragments were then cloned into the pAAV_159_SpCas9 and pAAV_100_SpCas9 constructs, respectively. Self-limiting sequences of the sgRNA_1295del were introduced 5' and 3 of the SpCas9 sequence using Gibson assembly.

Example 11-Whole-Genome Sequencing Analysis to Identify Off-Targets Genome-Wide Whole-genome sequencing was done commercially by BGI, China, on the BGISEQ-500 sequencing platform. Comprehensive next-generation sequencing (NGS) data analysis was carried out in-house in a laboratory using the CLC Biomedical Genomics Workbench (Qiagen).

Example 12-Determination of Recurrent Best Macular Dystrophy and ADVIRC Associated BEST1 Mutations Initially, the frequency of BEST1 mutations in Best macular dystrophy and ADVIRC patients tested at the Molecular Diagnostics Lab at the Institute of Human Genetics in Regensburg (mutation-based approach) was examined. While most of the mutations were non-recurrent, approximately 15% (17 out of 115) of all patients with autosomal dominant Best macular dystrophy carry an in-frame 3 bp deletion (TCA) at position 884-886 in exon 8 of the BEST1 gene that leads to an in-frame deletion of codon 295 (1295del). To target the 1295del-allele with SpCas9, the most widely used CRISPR-Cas nuclease (5-NGG-3'PAM recognition site), two out of four possible sgRNAs were suggested to be of high quality (scores>50=1. Criteria) with no off-targets predicted in the coding sequences of other genes (FIG. 1). sgRNA #1 (named sgRNA_1295del20nt) was chosen for further experimental evaluation as the 3 bp deletion resides within the sgRNA seed region (8-12 bases proximal to the PAM site=2. Criteria), a crucial sequence that specifically interacts with the target sequence. Mismatches beyond the first 10 nucleotides adjacent to the 5'-end of the PAM site are not well tolerated and significantly decrease targeting specificity.

Example 13-Identification of Common (>5%) SNPs within the BEST1 Genomic Locus To design a minimal set of allele-specific sgRNAs independent of the individual mutation (haplotype-based approach) a genotype imputation was performed based on SNP data released from the 1000 Genomes Project. In total, 1.191 SNPs across the BEST1 locus were found including a 15 kb flanking region at the 5' end (FIG. 2). Of these, 69 SNPs revealed allele frequencies>5% in the European population. 47 of the 69 SNPs were excluded from analysis as they were located in repetitive sequences or showed no favorable on- and off-target scores (score<50). In total, sgRNAs targeting opposite strands of each SNPs could be designed for 22 SNPs (FIGS. 2 and 3, Table 1). Five of the 22 SNPs are located within the BEST1 coding sequence (429exon2, 534exon3, 749exon10, 756exon10 and 759exon10).

TABLE 1

Identified SNPs within the BEST1 genomic locus after computational filtering process

| n | Internal ID | rs-ID | Genomic region | Nucleotide exchange | Frequency (EU) |
|---|---|---|---|---|---|
| 1 | 239 | rs2521572 | non-coding | G > T | 0.06 |
| 2 | 298 | rs972354 | non-coding | A > G | 0.11 |
| 3 | 387 | rs972354 | non-coding | C > T | 0.10 |
| 4 | 390 | rs972353 | non-coding | T > C | 0.29 |
| 5 | 417 | rs2736596 | non-coding | G > A | 0.05 |
| 6 | 429 | rs1800007 | coding | T > C | 0.29 |
| 7 | 517 | rs183176 | non-coding | A > C | 0.08 |
| 8 | 534 | rs110974 | coding | C > A | 0.08 |
| 9 | 542 | rs195165 | non-coding | A > T | 0.08 |
| 10 | 550 | rs195164 | non-coding | G > A | 0.22 |
| 11 | 553 | rs909268 | non-coding | A > T | 0.22 |
| 12 | 564 | rs760306 | non-coding | C > T | 0.22 |
| 13 | 581 | rs195161 | non-coding | G > T | 0.32 |
| 14 | 587 | rs741886 | non-coding | G > T | 0.08 |
| 15 | 631 | rs195160 | non-coding | G > T | 0.10 |
| 16 | 655 | rs195158 | non-coding | T > G | 0.10 |
| 17 | 716 | rs195156 | non-coding | T > C | 0.10 |
| 18 | 749 | rs149698 | coding | G > A | 0.32 |
| 19 | 756 | rs1800008 | coding | C > T | 0.23 |
| 20 | 759 | rs1800009 | coding | T > C | 0.35 |
| 21 | 772 | rs17185413 | non-coding | T > C | 0.24 |
| 22 | 798 | rs2668897 | non-coding | C > A | 0.08 |

Example 14-Identification of Frequent BEST1 Haplotypes in the European Population Haplotype frequencies of the European population based on the 22 SNPs identified were calculated by the Hapview software. This revealed 30 haplotypes at the BEST1 locus. Of these, the most frequent five haplotypes (>5%) account for almost ¾ of haplotypes found in the European population (FIG. 3).

Sanger sequencing of the selected 22 SNPs in the cohort of 11 hiPSC cell lines reprogrammed from Best macular dystrophy and ADVIRC patient-derived fibroblast samples established nine of the most common European haplotypes (FIG. 4). Six out of the eleven patients (PAT 1, 2, 5, 6, 7 and 9) harbor one or more heterozygous SNPs in the coding region and can therefore be targeted by a single sgRNA, while for patients 3, 4 and 5 a simultaneous delivery of two sgRNAs is needed for a CRISPR/Cas-induced allele deletion. For the remaining three patients a haplotype-based approach is not applicable as patients 10 and 11 were homozygous for all 22 SNPs and no coding or exon spanning SNPs were available for patient 8.

From the data, it was concluded that approximately 70% of Best macular dystrophy patients are eligible for a haplotype-based approach. To this end knowledge of the parental origin of the chromosomal BEST1 region is essential.

Example 15-Experimental Evaluation of in Silico Designed sgRNAs in HEK293T Cells To evaluate computationally designed sgRNAs for efficacy and allele specificity, a fluorescence-based assay (Mashiko et al., 2013) was adapted and a genomic fragment of 250-500 bp was cloned containing either the on-target or the non-target sequence between enhanced green fluorescent protein (EGFP) fragments of the pCAG-EGxxFP plasmid. The resulting target plasmid was co-transfected into HEK293 cells with the SpCas9-expressing px330 plasmid harboring the corresponding sgRNA. If the target sequence is cleaved by the endonuclease, homology dependent repair takes place to reconstitute the EGFP expression cassette (FIG. 5A) and the reconstituted EGFP fluorescence was quantified after 72h of transfection (FIG. 5B). In a first step, all sgRNAs with the natural 20 nt sgRNA sequence length (sgRNA_20nt) exemplified for sgRNA_581G20nt, sgRNA_581T20nt, sgRNA_749A20nt, sgRNA_749G20nt, sgRNA_756C20nt and sgRNA_756T20nt were analyzed. After microscopic inspection and plate reader measurements five of the six sgRNAs tested were identified showing a higher specificity to the on-target allele in comparison to the non-target site but still exhibited a too high degree of non-specific CRISPR/Cas9 cutting events at the non-target allele. Only sgRNA_581G20nt for SNP 581G demonstrated a remarkably high efficiency and specificity. In contrast, sgRNA_581T20nt for SNP 581T exhibited an unexpected strong fluorescence signal at the opposite allele thereby targeting the non-target allele much better than the on-target (FIGS. 5A and B). From these results, it was concluded that in many cases a single mismatch in a 20nt sgRNA sequence is well-tolerated and therefore not suitable to clearly distinguish the two DNA strands.

Example 16-Optimization of in Silico Designed sgRNAs in HEK293T Cells

To increase allele specificity two modifications were tested: (1) shortening of the sgRNA sequence length from 20 to 17 bp as truncation can increase sgRNA specificity (Fu et al., 2014) and/or (2) introducing a base mismatch into the sgRNA thereby creating a new single base pair mismatch to the on-target sequence and an additional second mismatch to the off-target allele. FIG. 6 displays the results exemplified for sgRNA 756C, 756T, 429C and 1295del. It was found that truncation of sgRNA 756C and 756T from 20 to 17 nt led to a considerable (FIG. 6A) or moderate (FIG. 6B) improvement of allele-specificity, whereas shortening of sgRNA 429C was rather ineffective (FIG. 6D). Furthermore and in agreement with recent findings (Zhang et al., 2016), the sgRNA sequence length also significantly affected Cas9 cleavage efficacy. While equal nuclease efficacy was observed for truncated sgRNA 756C17nt in comparison to the full-length sgRNA, a continuous decrease was found to about 40 percentage points for sgRNA 429C17nt (FIG. 6D). In contrast, for truncated sgRNAs 1295del18nt and 1295del17nt a substantial increase in Cas9 efficacy (FIG. 6C) was observed compared to the initial 20nt sgRNA. To increase allele-specificity for sgRNA 756T and 429C a single nucleotide exchange was consecutively introduced at various positions within the full-length sgRNA. While in sgRNA 429C an adenosine to thymine exchange at nucleotide position 20 (relative to the PAM recognition site) significantly increased allele specificity with comparably high Cas9 efficacy compared to the initial sgRNA 429C20nt, a cytosine nucleotide exchange at the same position or two other exchanges at position 19 almost depleted Cas9 efficacy (FIG. 6D). In contrast, for sgRNA 756T only base substitution guanine to cytosine at position 17 produced an optimum result. Of note, a nucleotide exchange within the sgRNA seed region at position 6 (sgRNA_756T20nt_(6) G>A) completely abolished Cas9 activity. This way, for 18 out of 19 sequence variants analyzed at least one sgRNA was defined revealing high allele specificity and efficacy. A list of all sgRNA sequences analyzed is given in Table 2.

Taken together, the results show that depending on the sgRNA nucleotide composition each sgRNA requires individual and highly sophisticated testing to reach optimal allele specificity without concomitant loss of efficacy.

TABLE 2

| | | | | | | | | |
|---|---|---|---|---|---|---|---|---|
| Optimized sgRNAs at the BEST1 genomic locus | | | | | | | | |
| Internal ID | rs-number | BEST1 locus | nucleo-tide | sgRNA sequence (5'-3') | sgRNA sequence* | Seq ID No | PAM sequence | in/del fre-quency● |
| 390 | rs972353 | non-coding | T | CAAGAAGGGACUAAGACA | 390T_18 nt | 1 | NGG | n.t. |
| | | | T | UACAAGAAGGGACUAAGACA | 390T_20 nt | 39 | NGG | n.t. |
| | | | C | ACAAAGGAGUCCUUGUCU | 390C_18 nt | 2 | NGG | n.t. |
| | | | C | CACAAAGGAGUCCUUGUCU | 390C_19 nt | 40 | NGG | n.t. |
| 429 | rs1800007 | exon 2 | T | AUUAAGAACUCGCCAUA | 429T_17 nt | 3 | NAG | 0.07 |
| | | | T | AGCUUAAGAACUCGCCAUA | 429T_19 nt_(17)A > C | 4 | NAG | 0.07 |
| | | | T | AAGAUUAAGAACUCGCCAUA | 429T 20 nt | 41 | NAG | n.t. |
| | | | C | UGUAGCAGAGCAGGAAGAUU | 429C_20 nt_(20)A > T | 5 | NGG | n.t. |
| | | | C | CUAGCAGAGCAGGAAGAUU | 429C_19 nt_(19)G > C | 6 | NGG | 0.25 |
| 534 | rs110974 | exon 3 | C | AAGGAAAUGGGGAUGAGC | 534C_18 nt | 7 | NGG | 0.50 |
| | | | C | GAAGGAAAUGGGGAUGAGC | 534C_19 nt | 42 | NGG | n.t. |
| | | | C | CGAAGGAAAUGGGGAUGAGC | 534C_20 nt | 43 | NGG | n.t. |
| | | | A | UAUUGCGACAGCUACAUA | 534A_18 nt | 8 | NAG | n.t. |
| | | | A | UGUAUUGCGACAGCUACAUA | 534A_20 nt | 44 | NAG | n.t. |
| 517 | rs183176 | non-coding | A | CCUUUGAAUGCAUCCAA | 517A_17 nt | 9 | NGG | 0.30 |
| | | | A | GAUCCUUUGAAUGCAUCCAA | 517A_20 nt | 45 | NGG | n.t. |
| | | | C | UUGGCUGCAUUCAAAGG | 517C_17 nt | 10 | NGG | 0.63 |
| | | | C | CCUUUGAAUGCAGCCAA | 517C_17 nt | 53 | NGG | 0.63 |
| | | | C | GAUCCUUUGAAUGCAGCCAA | 517C_20 nt | 46 | NGG | n.t. |

TABLE 2-continued

Optimized sgRNAs at the BEST1 genomic locus

| Internal ID | rs-number | BEST1 locus | nucleo- tide | sgRNA sequence (5'-3') | sgRNA sequence* | Seq ID No | PAM sequence | in/del fre- quency● |
|---|---|---|---|---|---|---|---|---|
| 542 | rs195165 | non- coding | A | GUCUAACUUCAGUUUCUC | 542A_18 nt | 11 | NGG | 0.37 |
|  |  |  | A | ACGUCUAACUUCAGUUUCUC | 542A_20 nt | 47 | NGG | n.t. |
|  |  |  | T | GUCUAACUUCAGUUUCAC | 542T_18 nt | 12 | NGG | 0.60 |
|  |  |  | T | ACGUCUAACUUCAGUUUCAC | 542T_20 nt | 48 | NGG | n.t. |
| 581 | rs195161 | non- coding | G | GAGGGUCUUCCGAGAGC | 581G_17 nt | 13 | NGG | 0.70 |
|  |  |  | G | CCUGAGGGUCUUCCGAGAGC | 581G_20 nt | 49 | NGG | n.t. |
|  |  |  | T | not allele specific |  |  |  |  |
| 749 | rs149698 | exon 10 | G | UGGGGCUGAGGGGCGUCUG | 749G_20 nt | 14 | NGG | 0.25 |
|  |  |  | G | UGGGGCUGAGGGGCGUCUGU | 749G_20 nt | 54 | NGG | 0.25 |
|  |  |  | A | UGGGGCUGAGGGGUGUCUG | 749A_20 nt | 15 | NGG | 0.35 |
|  |  |  | A | UGGGGCUGAGGGGUGUCUGU | 749A_20 nt | 55 | NGG | 0.35 |
| 756 | rs1800008 | exon 10 | C | GCUCUCAGAGAGCGAUG | 756C_17 nt | 16 | NGG | 0.05 |
|  |  |  | T | AUUACUCUCAGAGAGUGAUG | 756T_20 nt_ (17)G > A | 17 | NGG | n.t. |
|  |  |  |  | GCUCUCAGAGAGUGAUG | 756T_17 nt | 50 | NGG | n.t. |
| 759 | rs1800009 | exon 10 | T | UCAAGUGAGGAGGAAAACUG | 759T_20 nt | 18 | NGG | 0.30 |
|  |  |  | C | UCAAGUGAGGAGGAAAACCG | 759C_20 nt | 19 | NGG | n.t. |
|  |  | exon 8 | TCAdel | GAGCAGCUCAACCCCUU | 1295del_17 nt | 20 | NGG | 0.58 |
|  |  | exon 8 | TCAdel | GCAGAGCAGCUCAACCCCUU | 1295del_20 nt | 51 | NGG | 0.47 |
|  |  | exon 8 | TCAdel | AGAGCAGCUCAACCCCUU | 1295del_18 nt | 52 | NGG | n.t. | bold and underlined = nucleotide change introduced in reference sequence; * = sgRNAs tested for efficacy and specificity in a fluorescence-based assay in HEK293 cells; ● = sgRNAs tested in hiPSC-RPE cells; n.t. = not yet tested in hiPSC-RPE cells; NGG and NAG = PAM recognition site for SpCas9;
SEQ ID NO: 10 shows the reverse sequence of SEQ ID NO: 53. SEQ ID NO: 53 shows the correct sequence of sgRNA 517C_17 nt and is therefore preferred over SEQ ID NO: 10. In a further preferred embodiment of the present disclosure the reference to SEQ ID NO: 10 is replaced by a reference to SEQ ID NO: 53.
SEQ ID NO: 54 shows the correct sequence of sgRNA 749G_20 nt and is therefore preferred over SEQ ID NO: 14 lacking one nucleotide. In a further preferred embodiment of the present disclosure the reference to SEQ ID NO: 14 is replaced by a reference to SEQ ID NO: 54.
SEQ ID NO: 55 shows the correct sequence of sgRNA 749A_20 nt and is therefore preferred over SEQ ID NO: 15 lacking one nucleotide. In a further preferred embodiment of the present disclosure the reference to SEQ ID NO: 15 is replaced by a reference to SEQ ID NO: 55.

Example 17-Evaluation of Optimized sgRNAs in hiPSC-RPE Cell Lines Generated from Best Macular Dystrophy Patients Next, it was tested whether the initial results from the fluorescence-based assay could be verified in a cellular context. To this end, RNP complexes formed by recombinant SpCas9 and optimized sgRNAs were electroporated into patient-derived hiPSC-RPE cell lines heterozygous for selected SNPs or BEST1 mutation 1295del (see FIG. 4). After 48 hours cells were harvested and indel frequencies at on- and non-target strand were analyzed from 40-80 single clones via Sanger sequencing. Evaluation of 12 sgRNAs revealed no double-strand breaks (DSBs) at any of the non-target sites confirming high allele specificity for each of the sgRNAs tested. Of the 12 sgRNAs, nine showed reasonable indel frequencies ranging from 25 to 70% DSBs at the on-target allele. Only for sgRNAs 429T and 756T frequencies were rather low (7 and 5%, respectively). Another nine sgRNAs are under further evaluation. Of note, cleavage efficacies of most sgRNAs varied considerably and were hardly predictable from results obtained from co-transfection experiments in HEK293T cells. The latter point underscores the need to extensively test each sgRNA in advance of further application. A summary of sgRNAs analyzed in hiPSC-RPE cells is given in Table 2.

Example 18-Proof of Concept for the Allele-Specific Gene Editing Approach to Restore BEST1 Function To assess whether the developed gene editing approach can specifically suppress expression of mutant BEST1 transcript, hiPSCs from a heterozygous Best macular dystrophy patient harboring mutation I295del (+/1295del) were electroporated with SpCas9/sgRNA_1295del17nt RNPs. Subsequently, single cell populations were generated and analyzed for DSBs, two genome-edited clones (+/1295delcrispr #16 and +/1295delcrispr #19) with confirmed DSBs were selected for differentiation into CRISPR/SpCas9-edited RPE cell lines for further characterization. While cDNA samples of untreated patient cell lines revealed the presence of both, wildtype and mutant transcripts, the SpCas9-treated cDNA patient samples only revealed wildtype transcripts (FIG. 7A).

Then BEST1 localization, protein expression and anion transport function was explored in the SpCas9-treated hiPSC-RPEs in comparison to untreated and two control samples. While the untreated patient cell line exhibited a remarkable degree of mislocalized BEST1 protein, the two edited hiPSC-RPEs showed a clear cell surface expression representing the wildtype allele (FIG. 7B). This was mirrored by an increase of BEST1 protein expression in the SpCas9-edited cell lines that reached about half of the expression level compared to healthy controls (FIGS. 7C and D). Finally, BEST1 anion transport function was analyzed from YFP fluorescence recordings. The hiPSC-RPE cell lines were virally transduced with the yellow fluorescent protein (YFP)-based halide sensor YFP (H148Q/1152L) and seeded on black 96-well plates revealing a bright and uniform cell fluorescence highly sensitive to iodide ions (I–) (FIG. 7E). Application of I– leads to specific YFP quenching over time that is reversed by the addition of equimolar Cl–. Changes of fluorescence intensities can be monitored on a plate reader. After a six-week maturation period, hiPSC-RPEs were incubated with 72 mM I– containing solution and steady state YFP quenching was measured after 6 minutes. Subsequently, I– was replaced by equimolar Cl– solution and anion permeability was monitored by increasing fluorescence signal intensities as a result of BEST1-mediated I– exit in a time course up to 6 minutes. For both hiPSC-RPE cell lines from healthy controls a fast kinetic of increasing fluorescence signals up to ~ 40% was observed while the untreated VMD2-patient cell line remained rather flat as a result of impaired ionic flux. In contrast, the two CRISPR/SpCas9-treated cell lines showed increasing fluorescence kinetics similar to that of controls (FIG. 7F).

Taken together, immunocytochemical and functional characteristics of SpCas9-edited hiPSC-RPEs showed that allele-specific disruption of the 1295del transcript rescues the Best macular dystrophy phenotype implicating that haploinsufficiency of BEST1 wildtype transcripts is well tolerated.

Example 19-Genome-Wide CRISPR Off-Target Profiling by Whole-Genome Sequencing For future clinical application, the genome-wide identification of off-target effects is critical (Ran et al., 2013). To capture any genome-wide off-target sites of sgRNA_1295del17nt, genomic DNA from untreated and edited hiPSC-RPE samples was whole genome sequenced (30-fold coverage). Comprehensive NGS data analysis revealed many DNA reads with identical 5' or 3' ends at the on-target site but no off-target sites validating the specificity of truncated sgRNA_1295del17nt. A schematic presentation of the filtering process is shown in FIG. 8.

Example 20-Generation of a Self-Limiting "all-In-One" AAV Vector Transfer Plasmid In vivo translation of genome editing tools requires the efficient delivery of the Cas9/sgRNA machinery into post-mitotic RPE cells in vivo. The relatively large size of the gene encoding SpCas9 (~4.1 kb) when combined with the sgRNA scaffold is inefficient for packaging into a single AAV vector (FIG. 9A). To circumvent this restricted capacity, several AAV "all-in-one" vector constructs were generated and analyzed carrying a minimal CMV (100 and 159 bp, respectively) promoter for SpCas9 expression, a minimal H1 promoter (95 bp) and a shortened U6 promoter (99 bp), respectively, to drive sgRNA expression in combination with a minimal poly A signal sequence (49 bp) (Danzeiser et al., 1993; Myslinski et al., 2001; Senis et al., 2014) (FIG. 9B). The AAV transfer plasmid was generated via a successive cloning strategy and tested for cleavage efficacy in comparison to a dual vector system using a full-length RSV promoter for SpCas9 expression (vector 1) and the strong full-length U6 promoter for sgRNA expression (vector 2). In addition, SpCas9 self-limiting sequences was introduced into the vector according to Ruan et al. (2017) for two reasons: (I) sustained expression of SpCas9 is not required for gene editing and (II) prolonged expression of SpCas9 may increase off-target cleavage. Therefore, recognition sequences exemplified for sgRNA_1295del (sgRNAl295del target sequence plus corresponding PAM site) were added before and after the SpCas9 sequence. In this configuration, the sgRNA will guide SpCas9 for both, targeted genomic cleavage and cleavage of the AAV plasmid itself to delete the SpCas9 sequence and thereby limit the production of SpCas9 protein. To this end, cleavage efficiency of sgRNA_1295del in four different AAV promoter constructs was analyzed plus their corresponding self-limiting analogs in comparison to a dual vector application (FIG. 9C). It was found that truncated CMV_159 bp (mini159) showed similar or even higher SpCas9 activity when compared to a dual vector application, while CMV_100 bp (mini100) was rather inefficient. For sgRNA activity, "all-in-one" AAV constructs using a truncated U6 promoter showed stronger GFP expression when compared to a dual delivery and H1 promoter constructs. However, the introduction of self-limiting sequences 5' and 3' of the SpCas9 sequence significantly enhanced cleavage activity for all constructs tested, arguing for an additive effect of the CMV promoter on sgRNA_1295del expression. Consequently, for all sgRNAs listed in Table 2, self-limiting "all-in-one" AAV constructs are generated consisting of (I) a shortened U6 promoter for sgRNA expression (II) a CMV_159 bp promoter for driving SpCas9 expression and (III) self-limiting sgRNA sequences 5' and 3' of the SpCas9 sequence.

Example 21-Quantification of Allele-Specific CRISPR/SpCas9 Cleavage

To evaluate computationally designed sgRNAs for efficiency and allele specificity, we adapted a fluorescence-based assay and cloned a genomic fragment of ~500 bp containing either the on-target or the non-target BEST1 sequence between EGFP (enhanced green fluorescent protein) fragments of the pCAG-EGxxFP plasmid (Addgene, UK). The resulting target plasmid was co-transfected into HEK293 cells with the SpCas9-expressing plasmid pU6-(BbsI)_CBh-Cas9-T2A-mCherry (Addgene) and the corresponding sgRNA with varying sequence length (20-17 bp). If the target sequence is cleaved by the endonuclease, homology dependent repair takes place to reconstitute the EGFP expression cassette. Fluorescence intensities were quantified relative to basal fluorescence intensities of pCAG-EgxxFP. The results are shown in FIGS. 10 to 13.

Example 22-Evaluation of the Haplotype-Based Approach

To test the efficacy of the haplotype-based approach, two plasmids were co-transfected into fibroblasts from a Best disease patient heterozygous for SNP 581 (G to T) and SNP 749 G to A), whereby SNP 581G and SNP 749A reside on a single haplotype. Each plasmid carries a specific sgRNA molecule, one targeting SNP 581G and one targeting SNP 749A. In addition, the px458 plasmid carrying the sgRNA 581G-17nt sequence (SEQ ID NO: 13) expresses both, the SpCas9 and the red fluorescent protein mcherry (Addgene #64324), while the px458 plasmid carrying sgRNA 749A-20nt (SEQ ID NO: 55) expresses the SpCas9 as well as the green fluorescent protein GFP (Addgene #48138). Fibroblasts expressing both a green and a red fluorescence signal were sorted by FACS (Fluorescence Activated Cell Sorting). Mcherry- and GFP-positive cells are indicative to harbor a haplotype-specific indel formation.

To control for successful indel formation.

In a next step, genomic DNA was extracted from the mcherry- and GFP-positive cells. The DNA was amplified using defined primer pairs flanking the SNP 581 and 749 sites resulting in a 560 bp fragment when approximately 7 kb of DNA between SNP 581 and SNP 749 was successfully excised and rejoined by the cellular NHEJ repair mechanism.

REFERENCES

Boon, C.J., Theelen, T., Hoefsloot, E. H. et al. (2009) Clinical and molecular genetic analysis of best vitelliform macular dystrophy. *Retina* 29:835-847.

Brandl, C., Zimmermann, S. J., Milenkovic, V. M., Rosendahl, S. M., Grassmann, F., Milenkovic, A., Hehr, U., Federlin, M., Wetzel, C. H., Helbig, H. et al. (2014). In-Depth Characterisation of Retinal Pigment Epithelium (RPE) Cells Derived from Human Induced Pluripotent Stem Cells (hiPSC). *Neuromolecular Med.*

Danzeiser, D. A., Urso, O. and Kunkel, G. R. (1993). Functional characterization of elements in a human U6 small nuclear RNA gene distal control region. *Mol Cell Biol* 13, 4670-8.

Fu, Y., Sander, J. D., Reyon, D., Cascio, V. M. and Joung, J. K. (2014). Improving CRISPR-Cas nuclease specificity using truncated guide RNAs. *Nat Biotechnol* 32, 279-284.

Gao, X., Tao, Y., Lamas, V., Huang, M., Yeh, W. H., Pan, B., Hu, Y. J., Hu, J. H., Thompson, D. B., Shu, Y. et al. (2018). Treatment of autosomal dominant hearing loss by in vivo delivery of genome editing agents. *Nature* 553, 217-221.

Giannelli, S. G., Luoni, M., Castoldi, V., Massimino, L., Cabassi, T., Angeloni, D., Demontis, G. C., Leocani, L., Andreazzoli, M. and Broccoli, V. (2018). Cas9/sgRNA selective targeting of the P23H Rhodopsin mutant allele for treating retinitis pigmentosa by intravitreal AAV9.PHP.B-based delivery. *Hum Mol Genet* 27, 761-779.

Khan, K. N., Islam, F., Moore, A. T. et al. (2018) The fundus phenotype associated with the p.Ala243Val BEST1 mutation. *Retina* 38:606-613.

Koo, T., Yoon, A. R., Cho, H. Y., Bae, S., Yun, C. O. and Kim, J. S. (2017). Selective disruption of an oncogenic mutant allele by CRISPR/Cas9 induces efficient tumor regression. *Nucleic Acids Res* 45, 7897-7908.

Lee, W., Lee, J. H., Jun, S., Lee, J. H. and Bang, D. (2018). Selective targeting of KRAS oncogenic alleles by CRISPR/Cas9 inhibits proliferation of cancer cells. *Sci Rep* 8, 11879.

Long, C., Amoasii, L., Mireault, A. A., McAnally, J. R., Li, H., Sanchez-Ortiz, E., Bhattacharyya, S., Shelton, J. M., Bassel-Duby, R. and Olson, E. N. (2016). Postnatal genome editing partially restores dystrophin expression in a mouse model of muscular dystrophy. *Science* 351, 400-3.

Marquardt, A., Stohr, H., Passmore, L. A., Kramer, F., Rivera, A. and Weber, B. H. (1998). Mutations in a novel gene, VMD2, encoding a protein of unknown properties cause juvenile-onset vitelliform macular dystrophy (Best's disease). *Hum Mol Genet* 7, 1517-25.

Mashiko, D., Fujihara, Y., Satouh, Y., Miyata, H., Isotani, A. and Ikawa, M. (2013). Generation of mutant mice by pronuclear injection of circular plasmid expressing Cas9 and single guided RNA. *Sci Rep* 3, 3355.

Milenkovic, A., Brandl, C., Milenkovic, V. M., Jendryke, T., Sirianant, L., Wanitchakool, P., Zimmermann, S., Reiff, C. M., Horling, F., Schrewe, H. et al. (2015). Bestrophin 1 is indispensable for volume regulation in human retinal pigment epithelium cells. *Proc Natl Acad Sci USA* 112, E2630-9.

Monteys, A. M., Ebanks, S. A., Keiser, M. S. and Davidson, B. L. (2017). CRISPR/Cas9 Editing of the Mutant Huntingtin Allele In Vitro and In Vivo. *Mol Ther* 25, 12-23.

Myslinski, E., Ame, J. C., Krol, A. and Carbon, P. (2001). An unusually compact external promoter for RNA polymerase III transcription of the human HIRNA gene. *Nucleic Acids Res* 29, 2502-9.

Petrukhin, K., Koisti, M. J., Bakall, B., Li, W., Xie, G., Marknell, T., Sandgren, O., Forsman, K., Holmgren, G., Andreasson, S. et al. (1998). Identification of the gene responsible for Best macular dystrophy. *Nat Genet* 19, 241-7.

Rabai, A., Reisser, L., Reina-San-Martin, B., Mamchaoui, K., Cowling, B. S., Nicot, A. S. and Laporte, J. (2019). Allele-Specific CRISPR/Cas9 Correction of a Heterozygous DNM2 Mutation Rescues Centronuclear Myopathy Cell Phenotypes. *Mol Ther Nucleic Acids* 16, 246-256.

Ran, F. A., Hsu, P. D., Wright, J., Agarwala, V., Scott, D. A. and Zhang, F. (2013). Genome engineering using the CRISPR-Cas9 system. *Nat Protoc* 8, 2281-308.

Ruan, G. X., Barry, E., Yu, D., Lukason, M., Cheng, S. H. and Scaria, A. (2017). CRISPR/Cas9-Mediated Genome Editing as a Therapeutic Approach for Leber Congenital Amaurosis 10. *Mol Ther* 25, 331-341.

Smith, C., Abalde-Atristain, L., He, C., Brodsky, B. R., Braunstein, E. M., Chaudhari, P., Jang, Y. Y., Cheng, L. and Ye, Z. (2015). Efficient and allele-specific genome editing of disease loci in human iPSCs. *Mol Ther* 23, 570-7.

Takahashi, K., Tanabe, K., Ohnuki, M., Narita, M., Ichisaka, T., Tomoda, K. and Yamanaka, S. (2007). Induction of pluripotent stem cells from adult human fibroblasts by defined factors. *Cell* 131, 861-72.

Yamamoto, Y., Makiyama, T., Harita, T., Sasaki, K., Wuriyanghai, Y., Hayano, M., Nishiuchi, S., Kohjitani, H., Hirose, S., Chen, J. et al. (2017). Allele-specific ablation rescues electrophysiological abnormalities in a human iPS cell model of long-QT syndrome with a CALM2 mutation. *Hum Mol Genet* 26, 1670-1677.

Yardley, J., Leroy, B. P., Hart-Holden, N., Lafaut, B. A., Loeys, B., Messiaen, L. M., Perveen, R., Reddy, M. A., Bhattacharya, S. S., Traboulsi, E. et al. (2004). Mutations of VMD2 splicing regulators cause nanophthalmos and autosomal dominant vitreoretinochoroidopathy (VRCP). *Invest Ophthalmol Vis Sci* 45, 3683-9.

Zhang, J. P., Li, X. L., Neises, A., Chen, W., Hu, L. P., Ji, G. Z., Yu, J. Y., Xu, J., Yuan, W. P., Cheng, T. et al. (2016). Different Effects of sgRNA Length on CRISPR-mediated Gene Knockout Efficiency. *Sci Rep* 6, 28566.

The invention claimed is:

1. A sgRNA molecule comprising a targeting domain for specifically targeting a SNP in the BEST1 coding region of a pathologic allele, wherein said targeting domain consists of a sequence selected from the group consisting of SEQ ID NO: 6, 17, 20, 51 and 52 or a sgRNA molecule combination of a first and second sgRNA molecule each comprising a targeting domain for specifically targeting a SNP in the BEST1 gene coding or non-coding region of a pathologic allele, wherein:

(i) if the targeting domain of the first sgRNA consists of a sequence according to SEQ ID NO: 20 or 51-52, the targeting domains of the second sgRNA consists of a sequence according to SEQ ID NO: 1-19, 39-50 or 53-55;

(ii) if the targeting domain of the first sgRNA consists of a sequence according to SEQ ID NO: 1-2 or 39-40, the targeting domains of the second sgRNA consists of a sequence according to SEQ ID NO: 3-20 or 41-55;

(iii) if the targeting domain of the first sgRNA consists of a sequence according to SEQ ID NO: 3-6 or 41, the targeting domains of the second sgRNA consists of a sequence according to SEQ ID NO: 1-2, 39-40, 7-20 or 42-55;

(iv) if the targeting domain of the first sgRNA consists of a sequence according to SEQ ID NO: 7-8 or 42-44, the targeting domains of the second sgRNA consists of a sequence according to SEQ ID NO: 1-6, 39-41, 9-20 or 45-55;

(v) if the targeting domain of the first sgRNA consists of a sequence according to SEQ ID NO: 9-10, 45-46 or 53, the targeting domains of the second sgRNA consists of a sequence according to SEQ ID NO: 1-8, 39-44, 11-20, 47-52 or 54-55;

(vi) if the targeting domain of the first sgRNA consists of a sequence according to SEQ ID NO: 11-12 or 47-48, the targeting domains of the second sgRNA consists of a sequence according to SEQ ID NO: 1-10, 39-46, 13-20 or 49-55;

(vii) if the targeting domain of the first sgRNA consists of a sequence according to SEQ ID NO: 13 or 49, the targeting domains of the second sgRNA consists of a sequence according to SEQ ID NO: 1-12, 39-48, 14-20 or 50-55;

(viii) if the targeting domain of the first sgRNA consists of a sequence according to SEQ ID NO: 14-15 or 54-55, the targeting domains of the second sgRNA consists of a sequence according to SEQ ID NO: 1-13, 39-53 or 16-20;

(ix) if the targeting domain of the first sgRNA consists of a sequence according to SEQ ID NO: 16-17 or 50, the targeting domains of the second sgRNA consists of a sequence according to SEQ ID NO: 1-15, 39-49, 18-20 or 51-55; or (x) if the targeting domain of the first sgRNA consists of a sequence according to SEQ ID NO: 18-19, the targeting domains of the second sgRNA consists of a sequence according to SEQ ID NO: 1-17, 39-55, or 20.

2. The sgRNA molecule or the sgRNA molecule combination according to claim 1, wherein (xi) if the targeting domain of the first sgRNA consists of a sequence according to SEQ ID NO: 1 or 39, the targeting domains of the second sgRNA consists of a sequence according to SEQ ID NO: 13 or 49;

(xii) if the targeting domain of the first sgRNA consists of a sequence according to SEQ ID NO: 9 or 45, the targeting domains of the second sgRNA consists of a sequence according to SEQ ID NO: 11, 47, 13 or 49;

(xiii) if the targeting domain of the first sgRNA consists of a sequence according to SEQ ID NO: 11 or 47, the targeting domains of the second sgRNA consists of a sequence according to SEQ ID NO: 13 or 49;

(xiv) if the targeting domain of the first sgRNA consists of a sequence according to SEQ ID NO: 10, 46 or 53, the targeting domains of the second sgRNA consists of a sequence according to SEQ ID NO: 12 or 48; or (xv) if the targeting domain of the first sgRNA consists of a sequence according to SEQ ID NO: 13, the targeting domains of the second sgRNA consists of a sequence according to SEQ ID NO: 15 or 55.

3. The sgRNA molecule or the sgRNA molecule combination according to claim 1, wherein each targeting domain has a length of 17, 18 or 19 nucleotides.

4. A nucleic acid comprising a sgRNA domain, wherein the sgRNA domain consists of a sequence that encodes a sgRNA molecule according to claim 1, or a nucleic acid comprising a combination of two sgRNA domains, wherein the first sgRNA domain consists of a sequence that encodes a first sgRNA molecule of any sgRNA molecule combination according to any one of claims 1 to 3 and the second sgRNA domain consists of a sequence that encodes the second sgRNA molecule of said sgRNA molecule combination, or a nucleic acid combination of two nucleic acids, wherein (i) the first nucleic acid comprises a sgRNA domain consisting of a sequence that encodes a first sgRNA molecule of any sgRNA molecule combination according to any one of claims 1 to 3, and (ii) the second nucleic acid comprises a sgRNA domain consisting of a sequence that encodes the second sgRNA molecule of said sgRNA molecule combination.

5. The nucleic acid or the nucleic acid combination according to claim 4, wherein the nucleic acid or one or both nucleic acids of the nucleic acid combination further comprise a sequence encoding a Cas9 molecule.

6. A recombinant adenovirus-associated virus (AAV) comprising (a) a nucleic acid comprising a sgRNA domain according to claim 4, or (b) a nucleic acid combination according to claim 4, or a recombinant adenovirus-associated virus (AAV) combination of two recombinant adenovirus-associated virus (AAV), wherein (i) the first recombinant adenovirus-associated virus (AAV) comprises a first nucleic acid of any of the nucleic acid combination according to claim 4, and (ii) the second recombinant adenovirus-associated virus (AAV) comprises the second nucleic acid of said nucleic acid combination.

7. The recombinant AAV comprising a nucleic acid comprising a sgRNA domain or the recombinant adenovirus-associated virus (AAV) combination according to claim 6, wherein the AAV or one or both AAVs of the AAV combination further comprises a minimal CMV promoter sequence for Cas9 expression," a minimal H1 promoter sequence or a shortened U6 promoter for expression of the sgRNA domain in combination with a minimal poly A signal sequence.

8. The recombinant AAV or the recombinant adenovirus-associated virus (AAV) combination according to claim 6, wherein the AVV or one or both AAVs of the AAV combination comprise (i) a shortened U6 promoter sequence for promoting expression of the sgRNA domain, wherein the shortened U6 promoter is located upstream of the sgRNA domain;

(ii) a minimal CMV promoter sequence for promoting SpCas9 expression, wherein the CMV promoter sequence is located upstream of the sequence encoding the SpCas9 molecule; and (iii) a first and a second self-limiting sequence each comprising the targeting domain of the sgRNA molecule flanked by a PAM site sequence at its 3' end, wherein the first self-limiting sequence is located 5' of the SpCas9 sequence and the second self-limiting sequence is located 3' of the SpCas9 sequence.

9. The recombinant AAV or the recombinant adenovirus-associated virus (AAV) combination according to any one of claim 8, wherein the PAM site comprises the amino acid sequence "NGG" or "NAG".

10. The recombinant AAV or the recombinant adenovirus-associated virus (AAV) combination according to claim 7, wherein the shortened U6 promoter comprises a sequence as shown in SEQ ID NO: 30, the minimal CMV promoter comprises a sequence as shown in SEQ ID NO: 26, and/or the minimal poly A signal sequence has a sequence as shown in SEQ ID NO: 31.

11. A method of treating or preventing bestrophin-1-related retinopathies (BEST1-related retinopathies) comprising administering to a subject in need thereof a sgRNA molecule or the sgRNA molecule combination according to claim 1.

12. A method of treating or preventing bestrophin-1-related retinopathies (BEST1-related retinopathies) comprising administering to a subject in need thereof a nucleic acid or the nucleic acid combination according to claim 4.

13. The method according to claim 12, wherein the BEST1-related retinopathies are selected from the group consisting of Best macular dystrophy and autosomal dominant vitreoretinochoroidopathy (ADVIRC).

14. The method according to claim 11, wherein the sgRNA molecule,
　or the sgRNA molecule combination is formulated for subretinal, intravitreal or suprachoroidal injection.

15. The method according to claim 11, wherein the sgRNA molecule,
　or the sgRNA molecule combination is administered in an amount sufficient for editing of the target domain in the BEST1 gene to restore BEST1 channel function.

16. The method according to claim 11, wherein the BEST1-related retinopathies are selected from the group consisting of Best macular dystrophy and autosomal dominant vitreoretinochoroidopathy (ADVIRC).

17. A method of treating or preventing bestrophin-1-related retinopathies (BEST1-related retinopathies) comprising administering to a subject in need thereof a the recombinant AAV according to claim 6.

18. The method according to claim 17, wherein the BEST1-related retinopathies are selected from the group consisting of Best macular dystrophy and autosomal dominant vitreoretinochoroidopathy (ADVIRC).

19. The method according to claim 12, wherein the nucleic acid is formulated for subretinal, intravitreal or suprachoroidal injection.

20. The method according to claim 17, wherein the recombinant AAV is formulated for subretinal, intravitreal or suprachoroidal injection.

21. The method of claim 5, wherein the sequence encoding a Cas9 molecule is a SpCas9 molecule.

22. The method of claim 7, wherein the sequence encoding a Cas9 molecule is a SpCas9 molecule.

23. The method of claim 11, wherein the bestrophin-1-related retinopathy (BEST1-related retinopathy) is autosomal dominant BEST1-related retinopathy.

24. The method of claim 12, wherein the bestrophin-1-related retinopathy (BEST1-related retinopathy) is autosomal dominant BEST1-related retinopathy.

25. The method of claim 17, wherein the bestrophin-1-related retinopathy (BEST1-related retinopathy) is autosomal dominant BEST1-related retinopathy.

* * * * *